(12) United States Patent
Guenther et al.

(10) Patent No.: US 8,790,874 B2
(45) Date of Patent: Jul. 29, 2014

(54) DEVICE FOR INVESTIGATION OF A FLOW CONDUIT

(76) Inventors: Axel Guenther, Toronto (CA); Steffen-Sebastian Bolz, Toronto (CA)

( * ) Notice: Subject to any disclaimer, the term of this patent is extended or adjusted under 35 U.S.C. 154(b) by 88 days.

(21) Appl. No.: 12/999,943

(22) PCT Filed: Jun. 17, 2009

(86) PCT No.: PCT/CA2009/000852
§ 371 (c)(1),
(2), (4) Date: May 2, 2011

(87) PCT Pub. No.: WO2009/152618
PCT Pub. Date: Dec. 23, 2009

(65) Prior Publication Data
US 2011/0287469 A1 Nov. 24, 2011

Related U.S. Application Data

(60) Provisional application No. 61/073,244, filed on Jun. 17, 2008.

(51) Int. Cl.
*C12Q 1/68* (2006.01)
*A01N 1/00* (2006.01)

(52) U.S. Cl.
USPC ........................................ 435/6.1; 435/284.1

(58) Field of Classification Search
USPC ............................................. 435/6.1, 284.1
See application file for complete search history.

(56) References Cited

U.S. PATENT DOCUMENTS

| | | | |
|---|---|---|---|
| 4,212,297 A | 7/1980 | Johnson, Jr. et al. | |
| 5,167,630 A | 12/1992 | Paul | |
| 5,494,822 A * | 2/1996 | Sadri | 435/284.1 |
| 5,527,290 A | 6/1996 | Zadini et al. | |
| 5,922,687 A | 7/1999 | Mann et al. | |
| 6,074,368 A | 6/2000 | Wright | |
| 6,991,628 B2 | 1/2006 | Vito et al. | |
| 7,011,623 B2 | 3/2006 | Clerin et al. | |
| 8,389,271 B2 * | 3/2013 | Wright et al. | 435/284.1 |
| 2004/0044268 A1 | 3/2004 | Vito et al. | |
| 2009/0220948 A1 | 9/2009 | Oviso et al. | |
| 2010/0112542 A1 | 5/2010 | Wright et al. | |

FOREIGN PATENT DOCUMENTS

| | | |
|---|---|---|
| CN | 101184983 A | 10/2007 |
| JP | 2004/093553 A | 3/2004 |
| JP | 2006/526796 A | 11/2006 |
| WO | 03078606 | 9/2003 |
| WO | 2006/065739 A2 | 6/2006 |
| WO | 2006065739 | 6/2006 |
| WO | WO 2006/065739 A2 | 6/2006 |
| WO | 2007/112192 A2 | 10/2007 |
| WO | 2009042639 | 4/2009 |

OTHER PUBLICATIONS

PCT International Search Report, Aug. 20, 2009.
Bolz, Steffen-Sebastian, Susanne Pieperhoff, Cor De Wit, andr Ulrich Pohl. Intact endothelial and smooth muscle function in small resistance arteries after 48 hours in vessel culture, H1434-1439, The American Physiological Society, 2000, Munich, Germany.
Bolz, Steffen-Sebastian, Ulrich Pohl. Highly effective non-viral gene transfer into vascular smooth muscle cells of cultured resistance arteries demonstrated by genetic inhibition of sphingosine-1-phosphate-inducted vasoconstriction. 400-405, Aug. 8, 2003, Munich, Germany.

* cited by examiner

*Primary Examiner* — Karen Cochrane Carlson
*Assistant Examiner* — Natalie Moss
(74) *Attorney, Agent, or Firm* — Dority & Manning, PA

(57) ABSTRACT

A device for investigation of a flow conduit comprising: a base; and a module formed in the base, the module comprising: a main channel for the flow conduit, the main channel having a loading inlet for loading the flow conduit; a culture chamber in the main channel for at least one of perfusion and superfusion of the flow conduit; at least two fixation lines in communication with the main channel for providing fixation of the flow conduit at at least two fixation locations along the length of the flow conduit.

16 Claims, 31 Drawing Sheets

A  B

Bottom Layer

Top layer

Bottom Layer    Top Layer    Close-Up

Bottom Layer   Top Layer   Close-Up

DEVICE FOR INVESTIGATION OF A FLOW CONDUIT

TECHNICAL FIELD

The present disclosure relates to devices for investigation of a flow conduit. In particular, this disclosure relates to devices, such as chip-based or lab-on-a-chip devices, that may be suitable for investigation of a small-sized flow conduit, such as perfusable soft material samples or small viable or non-viable biological vessel segments.

BACKGROUND

High blood pressure, or hypertension, is a deadly condition that is reaching epidemic proportions. The global burden of hypertension is expected to increase by 60% from 26.4% (972 million people) in 2000 to 29.2% (1.56 billion people) by 2025. [Kearney, P. M. et al., Lancet, 2005. 365(9455): p. 217-223]. Although hypertension is traditionally viewed as a disease of aging, it is now prevalent in young adults, with several genetic and lifestyle factors contributing to its incidence and severity. Hypertension is a major risk factor for many diseases, including heart disease, stroke, and kidney failure. Since even at present our understanding of hypertension still does not encompass its inherent complexity, the vast majority of hypertensive patients are treated symptomatically, rather than causally. Knowledge regarding hypertension should be advanced in order to improve this situation. There is a growing consensus that hypertension is primarily linked to an elevated peripheral vascular resistance originating primarily from small resistance arteries in the terminal parts of the vascular tree.

Current knowledge regarding blood vessel structure and function is primarily derived from experiments using large non-resistance arteries, which are more easily accessible. Unfortunately, functional differences exist between large conduit and small resistance arteries as well as between resistance arteries from different vascular beds. Small resistance vessels are understudied, largely due to the considerable technical skills required to handle them experimentally. Since a better understanding of mechanisms that regulate resistance artery structure and function is key to improved strategies to treat hypertension, technologies that facilitate the handling of resistance arteries are needed. Similar challenges arise in attempting other investigations with such small arteries, for example in researching structural responses to other stimuli such as pharmaceuticals. These challenges are also present in investigations of other similar flow conduits, such as small tubules found in the lungs, pancreas, and others.

Current methods and processes use cell-based screens, genetic analysis and pharmacological tools combined with animal models to identify, test and assess safety and efficacy of a potential drug product. Consequently, the process is relatively long and only approximately one in a thousand pre-clinical identifications achieves success before being proposed for human trials.

Current methods are often time consuming, require care and training for the investigator, and often result in a low percentage of useable vessels for investigation. There remains the challenge of providing an efficient and standardized way to investigate these small flow conduits. It would be useful for a solution to these challenges to be applicable to other biological flow conduits, and artificial or engineered flow conduits.

SUMMARY

It would be desirable to provide a device that allows for investigation of flow conduits which addresses at least some of the challenges described above. It would be desirable if such technology could be scalable. Also desirable is a method or device for monitoring these flow conduits for their responses to treatment, for example their response to a pharmaceutical compound.

This disclosure describes a device for investigation of a flow conduit. This device allows flow conduits, including small viable or non-viable biological conduits (e.g., resistance arteries) to be reversibly or irreversibly loaded, fixed and perfused under physiological conditions. This device may allow fixation and perfusion of human-, animal-, and plant-derived flow conduits or artificial conduits on a chip or microdevice, for example a microfluidics chip or a lab-on-a-chip device. This device may provide a relatively optimized microenvironment for functional analysis and organ culture of flow conduits, the automation of the relatively difficult conduit cannulation process, and the capability to perform routine studies with small and fragile conduits.

This device may allow structural and response testing of flow conduits, for example in the identification of treatment products. This device may be used to test flow conduits from animals, humans, plants, and other organisms. The flow conduits may be from any organ, and may include artificial or engineered conduits. A flow conduit may include conduits found in organisms, such as lipid tubules, engineered vessels, hollow fibers, arteries, arterioles, veins, venules, lymphatic vessels, intestines, vas deferens, ovaric tubes, bile ducts, bronchial tubes, bronchiole, trachea, or any other similar structures, as well as structures found in plants. The device may also allow for targeted or personalized treatment of either an individual or groups of individual by using their representative conduits in screening for or assessment of certain drugs, diseases, conditions, or treatments.

The device may be scalable and/or multiplexed, may be handled by relatively minimally trained personnel and may reduce the cost per experimental unit compared to other devices commonly used for these studies. By allowing uniform handling, regardless of the skill set of the user, this device may promote standardization. In contrast, previously developed conventional experimental procedures for resistance artery isolation and culture [e.g., as disclosed in Bolz S S et al., J Vasc Res, 2003. 40(4): p. 399-405; and Bolz S S et al., Am J Physiol Heart Circ Physiol., 2000. 279(3): p. H1434-9] typically require relatively highly skilled personnel trained in micro-dissection techniques and specialized equipment.

In some aspects there is provided a device for investigation of a flow conduit comprising: a base; and a module formed in the base, the module comprising: a main channel for the flow conduit, the main channel having a loading inlet for loading the flow conduit; a culture chamber in the main channel for at least one of perfusion and superfusion of the flow conduit; at least two fixation lines in communication with the main channel for providing fixation of the flow conduit at at least two fixation locations along the length of the flow conduit.

In some examples, there may be a plurality of modules formed in the base. In some examples, the modules may be arranged in series, and the modules may share a common main channel. In some examples, the modules may be arranged in parallel, and the modules may share a common culture chamber.

In some examples, the device may further comprise an actuator embedded in the base, and the actuator may create a deformation of the base at least between the two fixation locations.

In some examples, the device may further comprise a lysis chamber in the main channel, and the lysis chamber may be in series with the culture chamber and may be adapted to receive at least a portion of the flow conduit from the culture chamber.

In some examples, the at least two fixation lines may allow reversible or irreversible fixation of the flow conduit.

In some examples, the main channel may have an outlet for extracting the flow conduit for analysis.

In some examples, the module may accommodate flow conduits having diameters in the range of about 3 micrometers to about 2,000 micrometers, for example in the range of about 15 micrometers to about 300 micrometers.

In some examples, the flow conduit may have a length in the range of about 10 micrometers to about 1.5 centimeters.

In some examples, the device may contain active compounds that are released over time.

In some examples, the base may comprise a biodegradable material.

In some examples, the base may comprise a material selected from the group consisting of: polymers, biopolymers, glass, semiconductors, metals, ceramics, and combinations thereof. For example, the polymer may be selected from the group consisting of: poly(dimethylsiloxane), polystyrene, poly(methyl methacrylate), and combinations thereof. For example, the biopolymer may be selected from the group consisting of: fibrinogen, collagen, laminin, and combinations thereof. For example, the semiconductor may be selected from the group consisting of: silicon and gallium arsenide.

In some examples, the device may further comprise an interface adapted to interface with analytical equipment, such as bright field or fluorescence microscopy techniques, including fluorescence intensity and fluorescence lifetime-based imaging, with optical spectroscopy, on-chip lysis and mass spectrometry.

In some examples, the culture chamber may comprise a biopolymer.

In some examples, the device may be comprised of two or more layers, and each layer may provide at least a portion of the module or at least a portion of a channel connection to the module.

In some examples, the device may further comprise at least one of: a processor, a memory unit, or a temperature control unit.

In some aspects there is provided a method of investigating a flow conduit comprising: providing the device described above; loading the flow conduit into the main channel; fixing the flow conduit in the main channel, wherein at least a portion of the flow conduit is in the culture chamber; perfusing or superfusing the flow conduit with a physiological solution; and monitoring the flow conduit over time.

In some examples, the method may further comprise applying a biological factor to the flow conduit via the culture chamber and monitoring the flow conduit for a response.

In some examples, the method may further comprise analyzing the flow conduit using a technique selected from the group consisting of: bright field or fluorescence microscopy techniques, fluorescence intensity and fluorescence lifetime-based imaging, optical spectroscopy, on-chip lysis and mass spectrometry.

In some examples, fixing the flow conduit may comprise applying a pressure lower than that in the culture chamber via the fixation lines.

In some examples, fixing the flow conduit may comprise applying a bonding material via the fixation lines.

In some examples, the bonding material may be selected from the group consisting of: a polymer that cross-links upon exposure to light, a polymer that cross-links upon exposure to moisture, and a polymer that cross-links in response to temperature changes.

In some examples, the method may further comprise applying a mechanical stimulation to the flow conduit along the axial axis of the flow conduit.

In some examples, monitoring the flow conduit may comprise taking diameter measurements using an integrated optical technique.

In some examples, the method may further comprise lysing the flow conduit using an enzymatic method.

In some examples, the method may be for investigation of angiogenesis, wherein the flow conduit may be a blood vessel, and the method may further comprise the step of stimulating angiogenesis by at least one of: mechanically rupturing the outer smooth muscle cell layer, laser ablation, and administration of an angiogenic factor. For example, the angiogenic factor may be selected from the group consisting of: endothelial cell growth factor (ECGF), fibroblast growth factor (FGF), angiogen, low molecular weight endothelial mitogens, endothelial cell chemotactic factors, lipids, vascular endothelial growth factor (VEGF), and platelet-derived growth factor (PDGF).

In some examples, the method may further comprise perfusing the flow conduit with a fluid containing particles or molecules, and assessing transport of the particles or molecules through the wall of the flow conduit and toxicity.

In some examples, the flow conduit may have a diameter in the range of about 3 micrometers to about 2,000 micrometers, for example in the range of about 15 micrometers to about 300 micrometers.

In some examples, the flow conduit may have a length in the range of about 10 micrometers to about 1.5 centimeters.

In some examples, the flow conduit may be selected from the group consisting of: brain conduits, lung conduits, inner ear conduits, lipid tubules, engineered vessels, hollow fibers, arteries, arterioles, veins, venules, lymphatic vessels, intestines, vas deferens, ovaric tubes, bile duct, bronchial, bronchiole, tracheal conduits, ureter, urethra, pancreatic duct, and kidney tubules.

In some examples, the method may be used for investigation of blood-brain barrier, and the brain conduit may be a blood vessel from a microvascular network of a brain.

In some examples, the flow conduit may be a biological conduit having a disease condition selected from the group consisting of: infarcted, ischemic, inflamed, sclerotic, immune compromised, tumors-bearing, and metastatic.

In some examples, perfusion may be at a rate of about 0-500 ml/hr or superfusion may be at a rate of about 0-500 ml/hr.

In some examples, the monitoring may be performed automatically using a computing device.

In some examples, the method may further comprise transmitting monitored data to an external device for analysis.

The device may contain a plurality of modules (e.g., arranged in series or in parallel), and may additionally include a lysis chamber for lysing at least a portion of the flow conduit. This device may be useful investigation of structural and functional properties of small blood vessels. In addition, this device may be useful in investigation of angiogenesis and other conditions pertaining to blood vessels, as well as other biological or non-biological flow conduits. This device may be useful for personalized medicine, and for development of pharmaceutical products.

BRIEF DESCRIPTION OF THE DRAWINGS

Reference will now be made to the drawings, which show by way of example embodiments of the present disclosure, and in which.

DETAILED DESCRIPTION

A device for investigation of a flow conduit is described. This device may provide at least (i) a relatively optimized microenvironment for functional analysis and organ culture of biological flow conduits, (ii) automation of an otherwise relatively difficult vessel cannulation process, and (iii) a capability to routinely study very small and fragile conduits, such as resistance arteries. These may be important elements in the construction of a human microcirculatory-based hypertension database, fed by laboratories and hospitals worldwide. This device may provide a potentially effective means of establishing global standards in data collection from microvessels.

In general, this device has a base and a module etched, embedded, molded, laser-machined or otherwise formed in the base. The module comprises a main channel for the flow conduit, a culture chamber in the main channel for perfusion and/or superfusion of the flow conduit, and at least two fixation lines in communication with the main channel for fixing the flow conduit along its length. The main channel typically has a loading inlet for loading the flow conduit. In some examples, the loading inlet is connected to a loading well formed on the device, to facilitate loading of the flow conduit.

Figure 1:
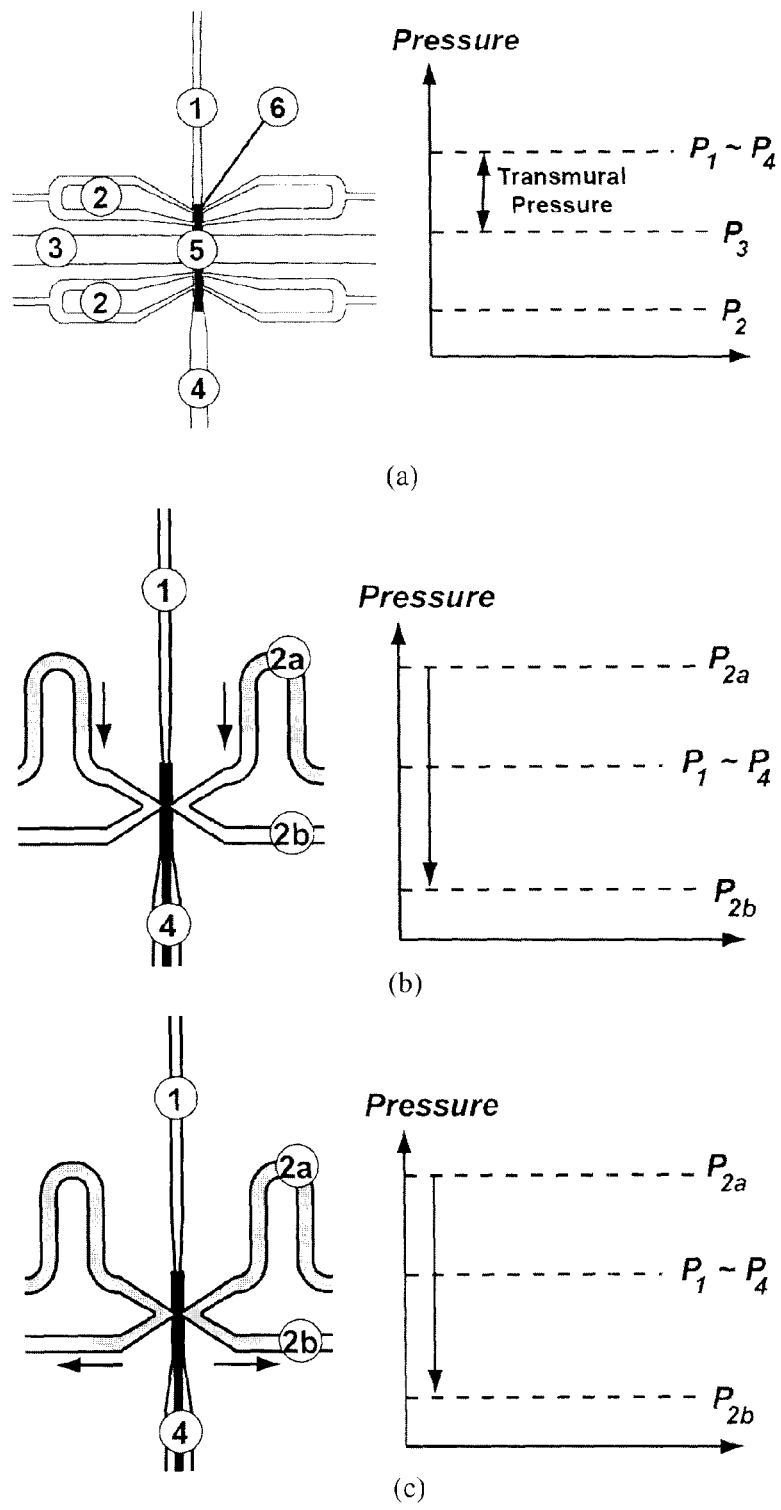
FIG. 1 illustrates schematically examples of loading a flow conduit in example embodiments of a module for a device for investigation of a flow conduit.

Reference is now made to FIG. 1, showing schematically example embodiments of a module for a device for investigation of a flow conduit, in particular showing example methods of fixating a flow conduit in a module. Also illustrated are charts showing the pressure at different points in the device.

a) shows a schematic diagram of an example embodiment for reversible fixation of the flow conduit, for example using a low pressure or suction method. As described above, the module has a main channel 1 with a loading inlet 4. There are two pairs of fixation lines 2, one pair located at each end of the culture chamber 5, for fixing the ends of a flow conduit 6, such as a small blood vessel. Here, a culture channel 3 may feed to and from the culture chamber 5, for example to provide an organ bath to the flow conduit 6. The culture channel 3 may allow for superfusion of the flow conduit 6. In other example embodiments, the culture chamber 5 may have an opening to the surroundings and may be fed directly through the opening, in which case the culture channel 3 may not be necessary. In this example, the main channel 1, loading inlet 4, fixation lines 2, and/or culture channel 3 may be microchannels.

The pressure profile beside the schematic diagram illustrates the relative pressures acting on the flow conduit 6. In this example, the loading inlet 4 is open to ambient pressure, $P_A$ (for example, the loading inlet 4 may be open to a petri dish from which the flow conduit 6 was loaded). Alternatively, the module may be in a closed configuration for which $P_4 \neq P_A$ may be realized (for example, the loading inlet 4 may be attached to the channel of another module, which will be described below).

For this example, the flow conduit 6 may be loaded by first closing the culture channel 3 and the fixation lines 2. A syringe pump controlling the vessel loading and perfusion processes may be connected to the main channel 1, opposite to the loading inlet 4, and operated in the "withdraw" or suction mode. The flow conduit 6 may be thus drawn toward its final position in the culture chamber 5. Once the flow conduit 6 has reached the desired position, its further movement may be prevented by a sufficient narrowing of the main channel 1 and/or by stopping the withdraw process through the main channel 1. The syringe pump may be then switched off. At both ends of the culture chamber 5, a suction pressure, which may be pre-defined, may be applied by the fixation lines 2 ($P_2$). This may be by connecting the fixation lines 2 to a liquid-filled tube that is connected to a hydrostatic pressure level lower than the culture chamber 5. Considering the typically short length of the flow conduit 6 and the slow perfusion rates, there may be typically negligible different in the pressures at each end of the blood vessel 6 (i.e., $P_1 \approx P_4$). While suction pressure may be applied at the fixation lines 2, the pressure difference (i.e., $P_1-P_2$ and $P_4-P_2$) may provide a relatively efficient and reversible fixation mechanism at both vessel ends. Thus, by low pressure, vacuum or suction is meant that the pressure applied at the fixation lines 2 is lower than the pressure at the inside and outside of the flow conduit (e.g., in the culture chamber). This method is not necessarily limited to the use of a vacuum or suction source. The flow conduit 6 may then be investigated. For example, the fixed flow conduit 6 may be superfused via the culture channel 3 and/or perfused via flow through the culture chamber 5 (e.g., flow from the inlet 4 through the main channel 1). A transmural pressure (e.g., $P_1-P_3$) may be established across the wall of the flow conduit 6. To release the flow conduit 6 from the module, the pressure in the fixation lines 2 may be increased to $P_1$. This may release the reversible seals at both vessel ends and the flow conduit 6 may be unloaded through the loading inlet 4.

Referring still to FIG. 1, b) and c) show an example of the device for irreversible loading of a flow conduit, for example fixation using polymerization or tissue adhesives. The module of b) and c) also has a main channel 1 with a loading inlet 4, a culture chamber 5 with culture channel 3, as described above. This module has fixation lines 2a and 2b that have a slightly different arrangement, which is described below.

Rather than fixing the flow conduit 6, such as a blood vessel, using a suction method as in a), the example of b) and c) may irreversibly fix the flow conduit 6 using an irreversible bonding agent, such as a polymer (e.g., a polymer that cross-links upon exposure to light, contact with moisture (such as a tissue adhesive), or temperature changes (such as fibrin or Matrigel™), or a solidifying chemical reaction that is otherwise induced. The uncured polymer or tissue adhesive may be introduced through fixation lines 2a (e.g., at a pressure exceeding $P_1$), for example at a constant flow rate with a syringe pump, resulting in an elevated inlet pressure. In this example embodiment, to prevent the situation where the culture chamber 5 is flooded with the bonding agent, a constant flow rate may be removed at fixation lines 2b. This may ensure that the flow conduit 6 is fixed only at one desired location. The bonding agent may be cured where it contacts the flow conduit 6, for example by using UV light on a photo-polymer, or simply by contact with tissue. Once curing starts, the feeding flow from fixation lines 2a may be stopped. A similar procedure may be used to fix both ends of the flow conduit 6. The flow conduit 6 may be then investigated. For this example embodiment, the flow conduit 6 may not be releasable from the module. For example b) and c) illustrate the introduction of a bonding agent, for irreversibly fixing the flow conduit 6. b) illustrates the introduction of a bonding agent (in grey), such as a tissue adhesive, into fixation lines 2a. c) illustrates the continued introduction of the bonding agent and its removal through fixation lines 2b. As shown in c), the bonding agent selectively contacts the flow conduit 6 only at distinct points, allowing the lumen of the flow conduit 6 to remain open. The bonding agent may cure or solidify at the point of contact, for example through a chemical reaction such as upon contact with moisture, thus irreversibly fixing the flow conduit 6.

This device may be suitable for the study of various flow conduits in animals and humans, including vessels isolated (e.g., through biopsies) from the brain, lung, inner ear and other organs. Aside from vessels, other flow conduits may be accommodated or studied using the device. Other possible flow conduits include lipid tubules, engineered vessel grafts, hollow fibers, arteries, arterioles, veins, venules, lymphatic vessels, intestines (e.g., duodenal, jejunal, ileal, and colon), vas deferens, ovaric tubes, bile duct, bronchial, bronchiole, tracheal conduits, ureter, urethra, pancreatic duct, and kidney tubules. Vessels found in plants, such as in the xylem, may also be studied using this device. Artificial or engineered flow conduits may also be studied, for example engineered blood vessels.

The flow conduits may range in size from about 3 micrometers to about 2,000 micrometers in diameter, more specifically from about 15 micrometers to about 300 micrometers, and from about 10 micrometers to about 1.5 centimeters in length. The conduits may be isolated from healthy or diseased tissue, for example to study vessels that are infarcted, ischemic, inflamed, sclerotic, immune-compromised, from tumors, or metastatic tissues.

The flow conduit may be perfused at a rate of about 0-500 ml/hr, or superfused at about 0-500 ml/hr. By "perfusion" is meant the movement of fluid through the lumen of the flow conduit; by "superfusion" is meant the movement of fluid along or over the outside of the flow conduit, whether axially along the length of the flow conduit or transversely around the circumference of the flow conduit. Both types of fluid movement may be present in the culture chamber. Both perfusion and superfusion may be useful in providing nutrients and other compounds (e.g., soluble factors, dyes or pharmaceutical agents) to and from the flow conduit in the culture chamber. In some cases, either perfusion or superfusion might be more preferable. The device may include sensors to sense and measure perfusion and/or superfusion. For example, pressure drop sensors may be integrated on the device (e.g., using piezoresistive pressure transducers), which may provide indication of perfusion and/or superfusion. Although the device is described as providing for superfusion and/or perfusion of the flow conduit, it should be understood that the device may also be used where there is neither superfusion nor perfusion, or where the flow conduit is placed under static flow conditions. The culture chamber may also be referred to as a "perfusion chamber" or "superfusion chamber", and the culture channel may also be referred to as a "perfusion channel" or "superfusion channel"; such references do not limit the use of these components of the device to only perfusion or superfusion, nor is the culture channel and culture chamber limited to delivering culture medium.

The module may be etched, embedded, molded or otherwise formed in the base using common fabrication methods such as replica molding, hot embossing, injection molding, lithography (e.g., X-ray lithography), electroplating, molding (e.g., LIGA), dry and wet etching, abrasive jet machining, and laser machining Other standard soft-lithographic techniques may also be suitable [for example, as described in Xia, Y. N. et al., Annual Review of Materials Science, 1998. 28: p. 153-184.]. Standard soft-lithographic techniques may be used in a variety of materials, for example silicones (e.g., poly(dimethylsiloxane) (PDMS)). Typically, the channels and structures of the module may be etched, embedded, molded or otherwise formed on the surface of one half of the base. That surface may then be bonded against the other half of the base, for example using techniques such as free-radical surface activation in a plasma and subsequent bonding, solvent bonding, compression bonding, or anodic bonding. Other common methods and variations for making microdevices may be suitable. The device may be made from single-layer designs, or from two- or multi-layer designs, in which each layer provides at least a portion of the module or at least a portion of a channel connection to the module. Multi-layer designs may be useful in reducing the necessary size of the device, and may be designed and manufactured using any suitable method, for example as described in U.S. Patent Publications Nos. 2001/0029983, 2001/0033796, 2001/0054778, 2002/0029814, 2003/0019833.

The device may be made from polymers (e.g., poly(dimethylsiloxane) (PDMS), polystyrene, poly(methyl methacrylate) (PMMA), and biopolymers such as fibrinogen, collagen, laminin and combinations thereof), glass, semiconductors (e.g., silicon or gallium arsenide), metals, ceramics, and combinations thereof. The device may be made from a biodegradable material. For example, the device may be made from a biopolymer, such as Matrigel™, which may be useful for investigation of angiogenesis.

Typically, at least a portion of the flow conduit, when fixed in the device, is viewable or detectable, so that changes to the conduit may be monitored and/or measured. The module is typically etched, embedded, molded or otherwise formed in the base, such that most of the module is enclosed (e.g., with the exception of inlets and outlets), however portions of the module may also be open. For example, the culture chamber may be at least partially open, so that an investigator can apply compounds to or otherwise stimulate the flow conduit directly.

In addition to the culture chamber, the module may include a lysis chamber (not shown). The lysis chamber may be provided in the main channel, in series with the culture chamber. The lysis chamber may be similar to the culture chamber, having respective fixation lines and a lysis channel. In practice, a flow conduit may be released from the culture chamber (e.g., where the flow conduit is reversibly fixed) and driven downstream (e.g., by applying a high pressure at the loading inlet) until it reaches the lysis chamber, where it may again be fixed by fixation lines. Alternatively, the lysis chamber may not have respective fixation lines, but may be large enough to accommodate the entire conduit. Alternatively, lysing may be formed in flow (i.e., without fixation of the conduit). The conduit may be lysed by introducing lysing compounds such as enzymes via the lysis channel. The resulting cellular and/or subcellular material may then be extracted from the device through an outlet in the main channel or through the loading inlet. Alternatively, lysing of the flow conduit may occur without using a lysis chamber, for example by introducing lysing compounds into the culture chamber. The lysis chamber may also receive only a portion of the flow conduit. For example, a portion of the flow conduit may be removed for lysing, such as removal by laser machining, suction or other suitable means. The lysis chamber may also be adapted to fit only a portion of the flow conduit, so that only the portion contained in the lysis chamber is lysed. Allowing only a portion of the flow conduit may be useful for investigating a certain desired portion of the flow conduit, for example only the smooth muscle cells of the flow conduit.

The device may have different depths for the various channels. For example, there may be two different channel depths at the conduit fixation points and the culture chamber. This may prevent unwanted contact between the center part of the conduit and the top or bottom walls inside the device.

The device may interface with analytical instruments, including microscopy (e.g., fluorescence or bright-field microscopy), mass spectrometry, or electrophoresis. The device may also be designed to interface with equipment for fluorescence intensity and fluorescence lifetime-based imaging, optical spectroscopy, on-chip lysis, or mass spectrometry. For example, the loading inlet or another outlet connected to the main channel may be designed to be easily connected to other analytical instruments, such that the flow conduit or lysed material in the device may be extracted directly into the analytical instrument.

By connecting syringe pumps (e.g., for the culture channel and/or inlet) to a computer (e.g., using serial ports: RS232, RS423, RS 485, firewire, USB, etc.), perfusion and/or superfusion processes may be automated. The response of the flow conduit (e.g., transmural pressure and/or artery contractile state) may be directly recorded on the device, for example by providing a processor (e.g., a microprocessor) and/or a memory unit on the device. This may allow mobile and self-contained investigation and analysis using the device. The device may include a temperature control unit (e.g., a thermoelectric or resistive element), or channels for a cross-flowing stream of constant-temperature fluid, may allow the temperature of the fixed flow conduit to be controlled (e.g., maintained at physiological levels) during investigation or culture of the flow conduit in the device. With a flow conduit fixed in the device, the temperature may be lowered, for example to 4° C. This may, for example, allow a flow conduit fixed in the device to be transported before or after being investigated. The dimensions of the device may be reduced, or other instruments and components may be added for additional functionality. Where the device has communication with a computer or other computing device, monitoring of the flow conduit may be performed automatically. Where the device includes a memory, recorded data, for example data from monitoring or investigation of the flow conduit, may be stored in the device. This stored data may be transmitted, wired or wirelessly, to an external device such as a workstation or external computer for analysis.

This device may be used for investigation of small flow conduits (e.g., resistance arteries) or large flow conduits (e.g., mesenteric arteries). Some flow conduits may require mechanical stimulation to remain viable. For example, mesenteric arteries need to be stretched longitudinally during culture (e.g., by up to 200 micrometers for a 1 mm long mesenteric artery segment). Such mechanical stimulation may be provided via the culture chamber. The ends of the flow conduit may be attached to manipulators, to mechanically stretch the flow conduit. Such manipulators may be integral to or external to the device. Alternatively or in addition, a mechanical actuator may be attached or embedded on the device.

In an example embodiment, the base of the device may be relatively compliant or elastic so that it is deformable. Stretching of the base in a direction aligned with the length of a fixed flow conduit may translate to mechanical stretching of the flow conduit. This stretching of the base may be provided by an integrated piezoelectric bending actuator located at one end of the flow conduit and designed to bend away from the flow conduit, thus causing a length-wise stretch. Such an actuator may be fabricated into the base of the device, or may be attached on the surface of the device. Other similar mechanical actuators may be used.

This device may provide complete environmental control over the flow conduit while maintaining its structural and functional integrity for extended periods of time (e.g., 10 days or more). Using this device, properties of flow conduits, including contractile, ionic, electrical, molecular and/or structural properties, may be monitored and investigated.

In some example embodiments, the device may include compounds to be administered to the flow conduit. For example, the device may include active compounds that are released over time into the culture chamber. In other examples, compounds in the device may be administered to a fixed flow conduit by manual or automated mechanisms.

EXAMPLES

Example of Single-Module Device

Figure 2:
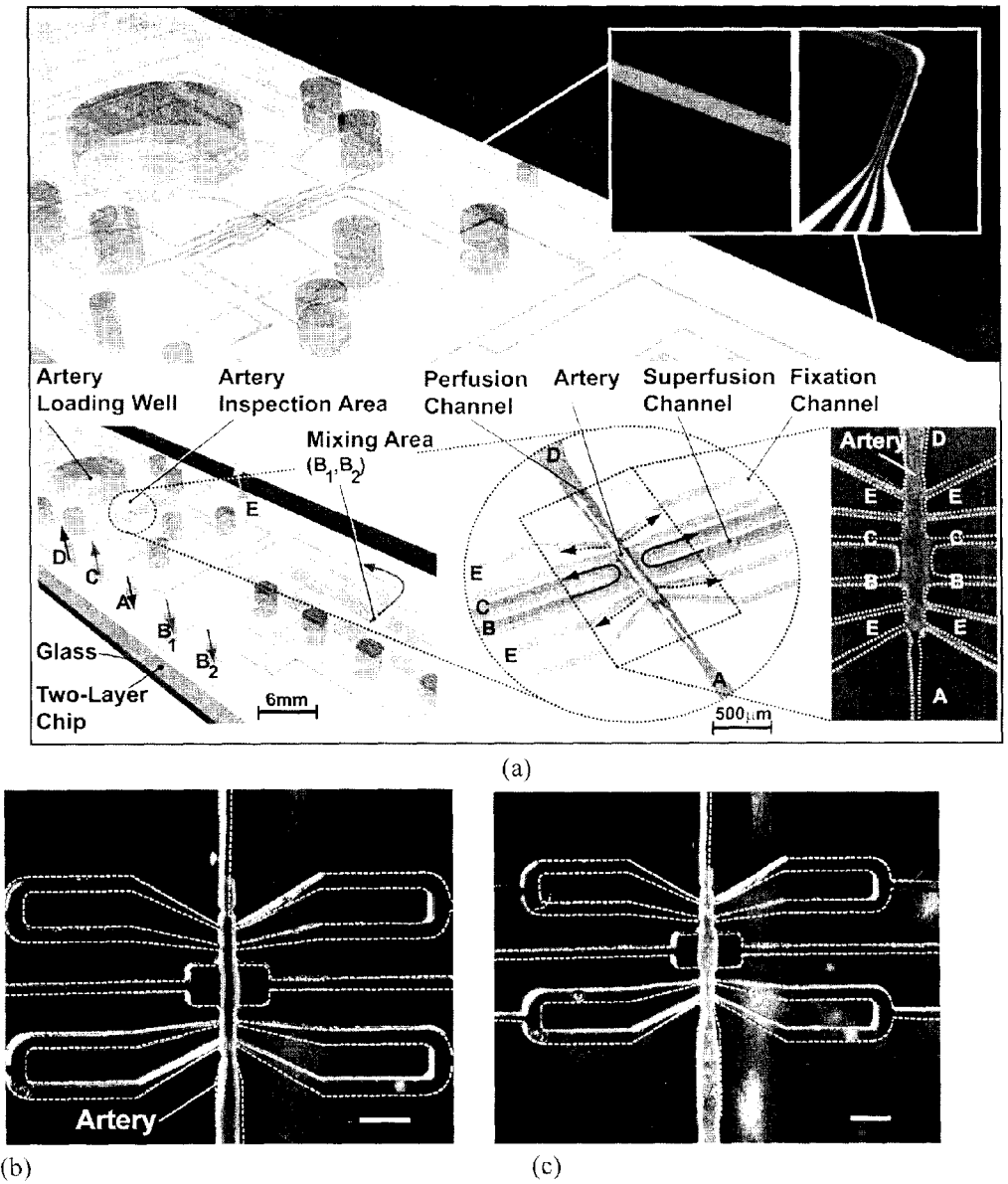
FIG. 2 shows images of an example embodiment of a device for investigation of a flow conduit.

Reference is now made to FIG. 2, showing images of an example embodiment of a device for investigation of a flow conduit, in use with an artery segment. In this example, the device was fabricated using multilayer soft-lithographic techniques. A resistance artery segment, approximately 1 mm in length, was introduced through an inlet, which may be connected to a loading well.

In this example, as shown in FIG. 2 a), the cylindrical artery segment was guided by pressure-driven flow through inlet "A" to the culture chamber, or artery inspection area. The artery was then fixed by applying a suction pressure at fixation lines "E". Subsequently, the artery segment was subjected to a microenvironment that mimicked physiological conditions by: (i) selectively superfusing the outside arterial wall with stream "B→C" (e.g., via the culture channel), (ii) perfusing the inside of the artery (i.e., lumen) with stream "A→D" (e.g., via the main channel), (iii) controlling the differential pressure across the arterial wall and (iv) adjusting the temperature to 37° C. Flow rates, pressures and compositions of the superfusing/perfusing streams could be independently adjusted. Crosstalk between the perfusion and superfusion lines was prevented by the fixation lines "E".

Referring still to FIG. 2, b) shows the device right after a previously isolated vessel or vessel segment is loaded into the culture chamber. Note that the vessel is pressurized and is still filled with blood. Pressurization to 100 mmHg initiated flow through the lumen of the vessel so that over time, the intraluminal blood was replaced by saline solution. c) shows the blood vessel with an open lumen after being perfused with saline and after a defined transmural pressure was applied. In this example, the device is also referred to as a chip, and the culture chamber is also referred to as an organ bath (OB).

This example embodiment of the device has outer dimensions of 75 mm (L)×25 mm (W)×4 mm (H), which is typically a size that allows inspection with common upright or inverted brightfield or fluorescence microscopes. Standard soft-lithographic techniques were used to translate microchannel designs from computer-aided design (CAD) files to printed transparency masks. Spincoated layers of negative photoresist (in this example, SU8-25™ and SU8-2050™, from MicroChem, Newton, Mass.) were pre-baked, exposed using the transparency masks, post-baked and subsequently developed. The inverse microchannel patterns were transferred to poly(dimethylsiloxane) molds. The optically transparent elastomeric mold was peeled off the master, cut, bonded to another elastomer layer or a pre-cleaned glass slide using an $O_2$ plasma. Multi-layer lithography allowed accommodation of two different channel depths at the fixation points and the culture chamber. Unwanted contact between the center part of the artery and the top/bottom walls of the device was thereby prevented.

Device fabrication is not limited to PDMS/glass as the structural materials, nor soft lithography as the microfabrication method. Any suitable materials and methods for microfabrication, as commonly known, may be used. Alternatively, the device may be fabricated using semiconductor materials, for example silicon using established bulk silicon machining techniques. Fabrication using glass may be accomplished by using wet and/or dry etching as well as laser machining techniques. Fabrication using a wide range of polymers including biocompatible and degradable polymer matrices may also be possible. Possible polymer device fabrication techniques include replica molding, hot embossing, injection molding, abrasive jet and laser machining.

In this example, the device was connected to 1/16" outer diameter (OD) polymer (e.g., Tygon®, PEEK, Teflon®) tubing comprising fluid perfusion, superfusion and waste lines through either an epoxy connection or a reversible manifold (e.g., a compression seal). The 1/16" OD polymer tubes were further connected with reversible fluidic unions (such as from Upchurch Scientific, Oak Harbor, Wash.) in order to conveniently remove the device from its connections to fluid-filled vials and/or manually controlled syringe pumps. The different fluid lines allowed for loading the flow conduit into the device, for providing perfusion through the inside of the flow conduit and superfusion of the conduit's outside wall in the culture chamber.

An example process of loading a flow conduit, in this case an artery, into this example embodiment of the device is now described. The device was initially flushed with a Bovine serum albumin (BSA) solution to prevent any unwanted adhesion of arteries to the walls of the main channel or culture chamber. Previously isolated resistance arteries (typically 1-2 mm long and 30-200 micrometers in diameter) were loaded into the device through a 200 micrometers wide and 150-200 micrometers deep loading inlet (e.g., where the device layout does not include a loading well) or from a loading well (e.g., where the device layout does include a loading well connected to the inlet). As an alternative to the reversible fixation of the artery used here, an irreversible fixation method may be used, as discussed above.

Upon fixation (e.g., using a reversible fixation method), the lumen of the artery was perfused by operating a syringe pump, connected to an inlet of the culture channel, in the perfusion mode. By connecting the inlet and outlet of the culture channel to different hydrostatic pressure levels, a flow through the culture chamber was achieved while maintain a defined transmural pressure difference across the wall of the artery. A flow through the culture chamber was achieved while maintaining a defined transmural pressure difference (i.e., $P_1-P_3$ in FIG. 1) by superfusing the culture chamber with a second syringe pump that operates in the perfusion mode, connected at the inlet of the culture channel. The outlet of the culture channel was thus led to a reduced hydrostatic pressure level. The artery interior and exterior walls were subjected to a defined transmural pressure and perfused with 3-(N-morpholino)propanesulfonic acid (MOPS buffer) containing defined concentrations of active molecules.

Figure 3:
FIG. 3 shows images of an example embodiment of a device for investigation of a flow conduit loaded with an artery.
Figure 3:
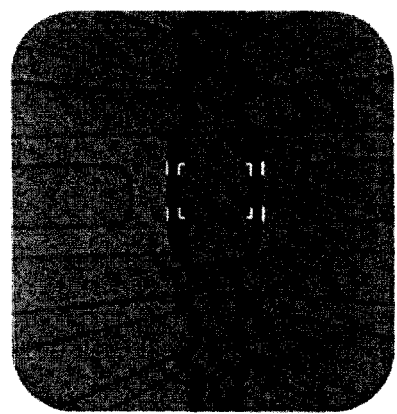

FIG. 3 shows images of an example embodiment of the device loaded with an artery. a) shows a mesenteric artery cannulated on glass micropipettes, held in place with sutures, and pressurized to 45 mmHg, using a conventional method. b) shows the mesenteric artery loaded into the culture chamber of an example device, pressurized to 45 mmHg, and held in place with suction applied via the fixation lines, which in this example are syringe-controlled low pressure channels.

Figure 4:
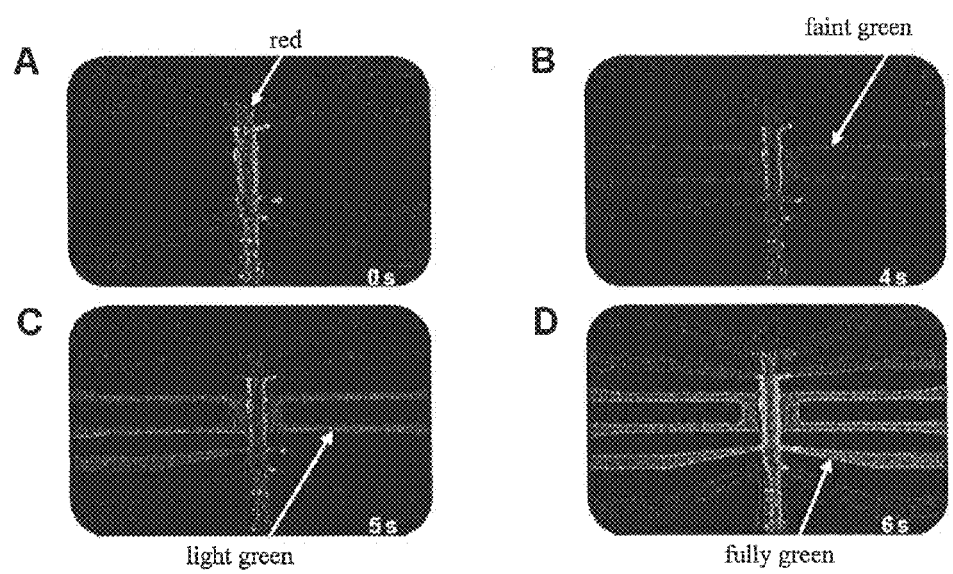
FIG. 4 shows images of an example embodiment of a device for investigation of a flow conduit used in perfusion of an artery.

FIG. 4 shows images of an example embodiment of the device demonstrating its use in perfusion of an artery. A resistance artery was loaded into the device and perfused with rhodamine dye, which shows red, through the lumen of the artery, and superfused with fluorescein dye, which shows green, in the culture bath. a) shows the artery at a baseline level of fluorescein. At 0 seconds, a syringe pump was used to infuse the artery with fluorescein at a flow rate of 4 mL/h. b) shows the artery at 4 seconds, when the fluorescein reaches the extra lumenal space. c) shows the artery at 5 seconds, when the artery is further exposed to the fluorescein. d) shows the artery at 6 seconds, when the artery is fully bathed in fluorescein. These images also demonstrate a separation of the fluids flowing in the vessel's intralumenal space (i.e., perfusion) from those outside of the vessel (i.e., superfusion).

Example Layouts

Certain designs and layouts have been prepared for this device and are shown in the figures described below. Where appropriate, the modules are enlarged to show details. These examples are for the purpose of illustration only and are not intended to be limiting.

In the examples described here, where there are two or more layers, external connections (e.g., to syringe pumps or low pressure sources) are indicated with a hole having an "X" and connections between upper and lower layers are indicated with a hole. In these schematics, inlets and outlets to the culture chamber may be referred to as "organ bath" or "perfusion" or "drain", inlets and outlets to the fixation lines may be referred to as "suction". In no way do any of these labels limit the possible connections and functions of these inlets and outlets or their various channels. For example, an inlet labeled as "suction" may be used to apply suction for reversible fixation of the flow conduit, but may also be used to administer a bonding material for irreversible fixation of the flow conduit.

Although not shown, the device may have a multi-layer layout in which one or more etched channels or chambers in the multiple layers are touching—that is, the channels or chambers of the upper and lower layers are not separated, but are continuous between the layers. This may provide for some deeper channels or chambers while keeping other channels or chambers on the device relatively shallow. A variation on this design may allow for even deeper chambers and/or channels by increasing the number of layers to three or more.

Figure 5:
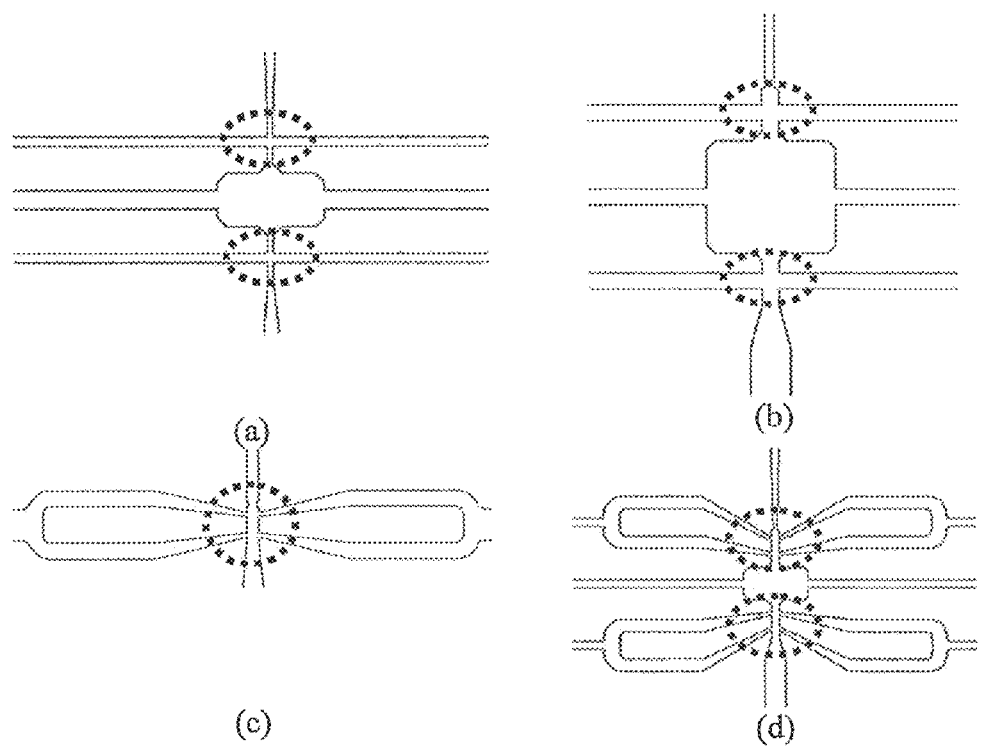
FIG. 5 illustrates schematically examples of fixation of flow conduits in example embodiments of a device for investigation of a flow conduit.

FIG. 5 illustrates schematically examples of fixation of flow conduits in example embodiments of the device. Here, reversible fixation techniques are demonstrated, with dashed circles marking the fixation locations. a) and b) show examples of designs having single fixation lines at each end of the culture chamber. c) and d) show examples of designs having multiple fixation lines at each of the culture chamber.

Figure 6:
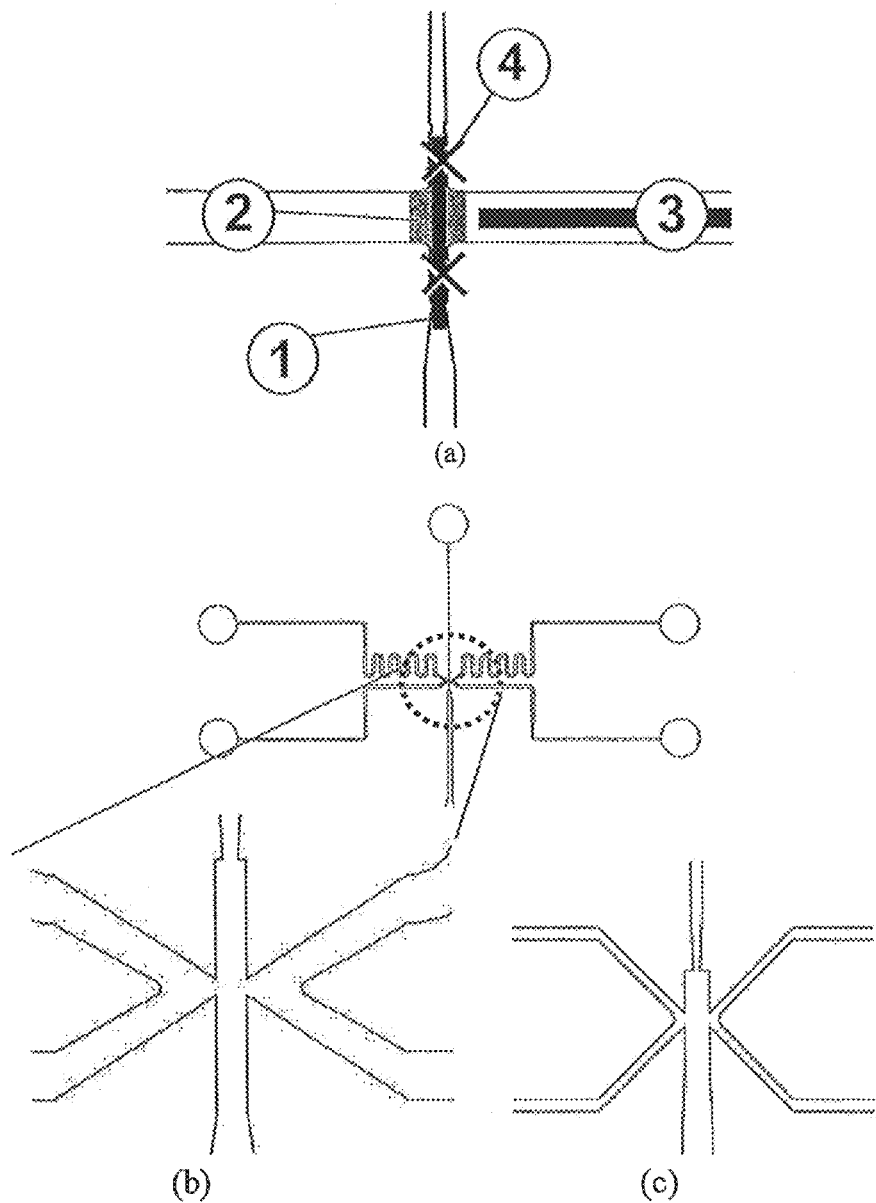
FIG. 6 illustrates schematically another example of fixation of flow conduits in example embodiments of a device for investigation of a flow conduit.

FIG. 6 is a schematic of an example device layout in which a flow conduit may be irreversibly fixed in the device. In particular, in a), the flow conduit (1) is reversibly fixed at both ends (4) so that the inside and outside areas of the conduit are separated from each other. At the outside areas, the flow conduit may further be embedded with a polymer (2). Focused light may be guided, for example through an embedded waveguide or optical fiber, and focused onto one section of the flow conduit. This arrangement may be useful for the selective removal and subsequent analysis of samples from the flow conduit, and may also be useful for studying the formation of vascular networks in healthy and diseased blood vessels at defined conditions, as will be discussed in further detail below.

Figure 7:
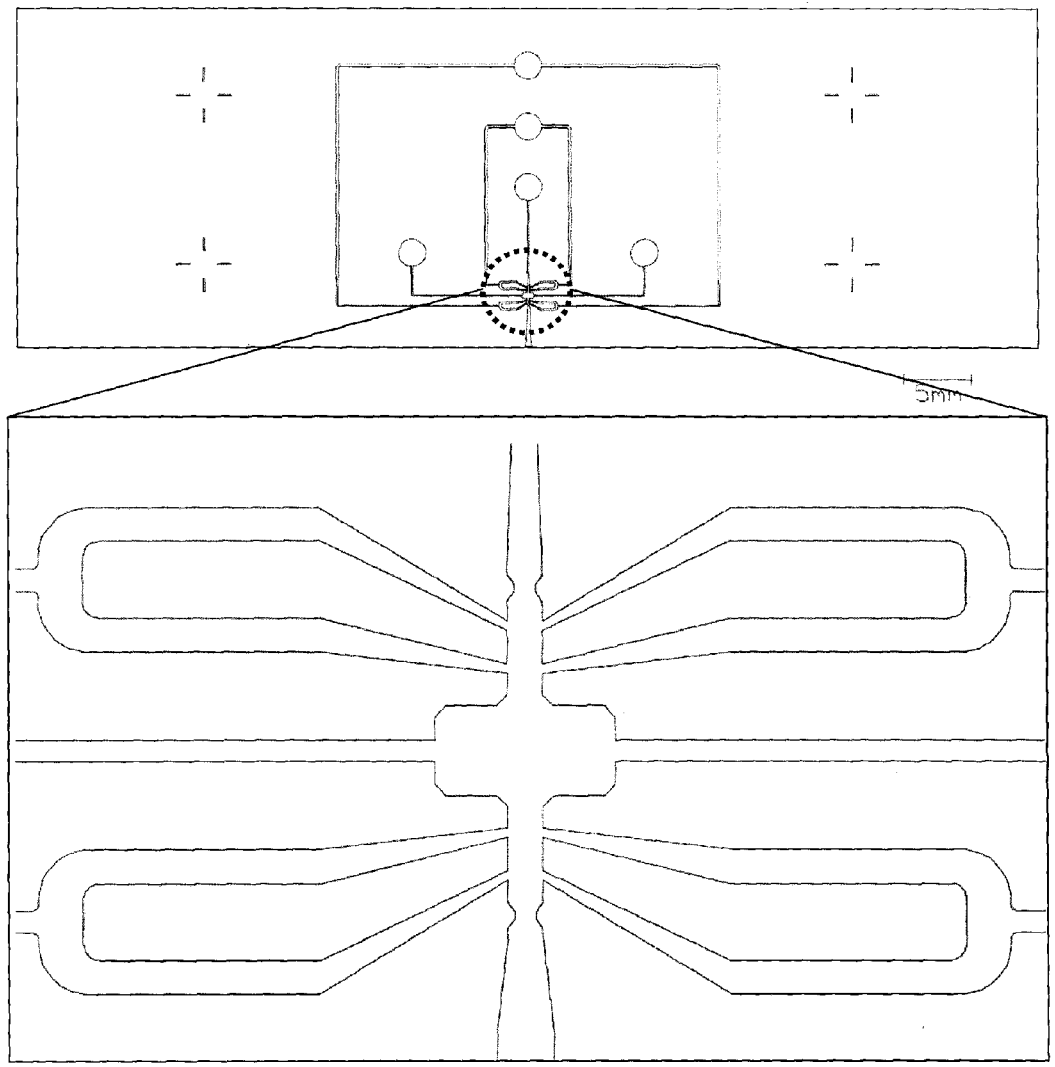
FIGS. 7-24 illustrate example embodiments of a device for investigation of a flow conduit having different layout designs.

FIG. 7 is a schematic of an example device layout, showing a single-layer layout without a loading bath. The flow conduit enters the device through the main channel that extends to the device bottom corner. The two fixation lines may be individually or separately accessed or addressable. There is one culture channel for a superfusion stream and one inlet for a perfusion stream. The flow rates and pressures of both streams may be separately adjusted/controlled. The superfusion stream flows across the flow conduit.

Figure 8:
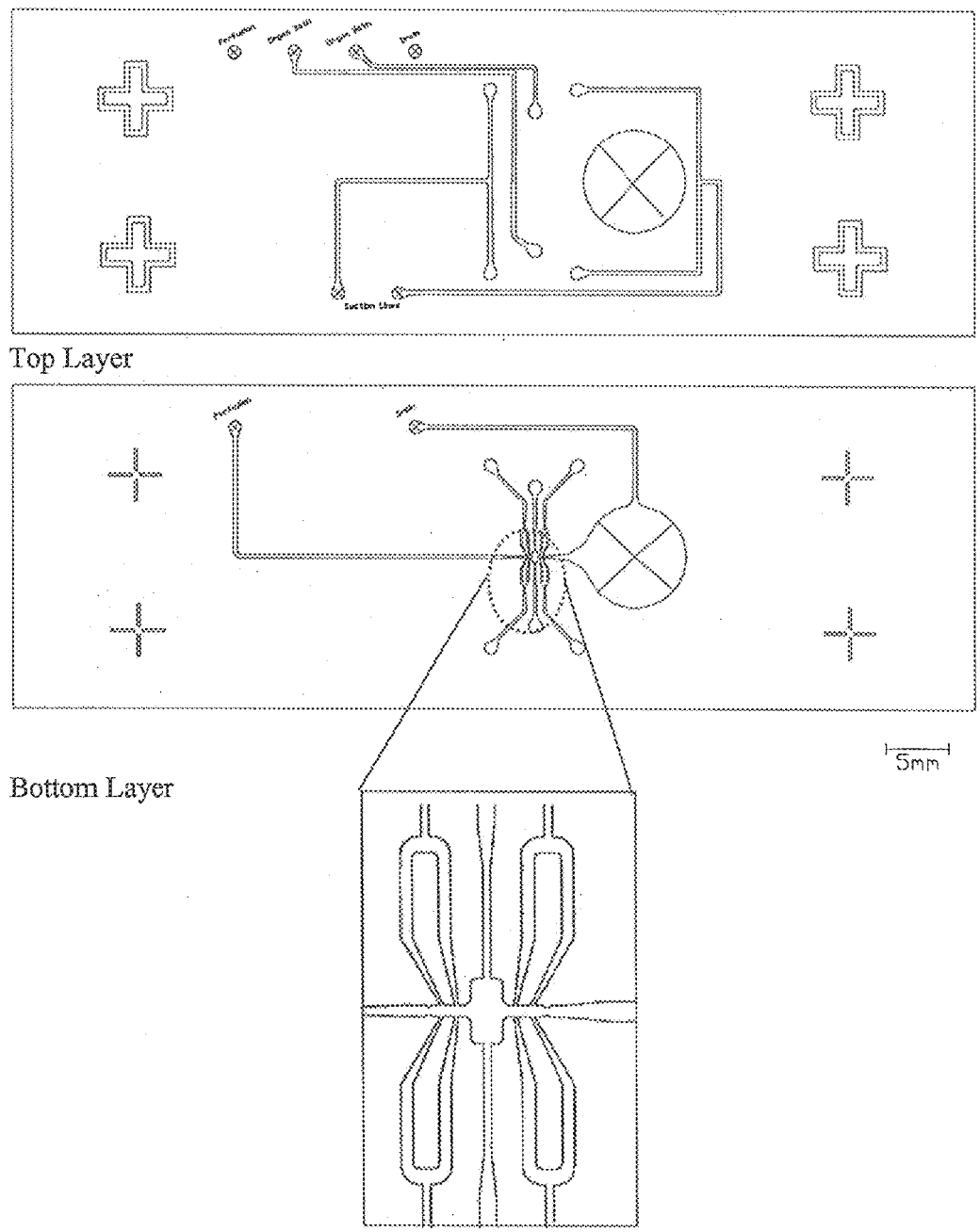

FIG. 8 is a schematic of an example device layout, showing a two-layer layout with a loading bath for loading a flow conduit. The upper image shows the top fluidic layer, and the bottom image shows the bottom fluidic layer of the device. The flow conduit enters the bottom layer of the device through a loading well into the main channel. The two fixation points at each end of the module are individually addressable. There is one culture channel for a superfusion stream and one inlet for a perfusion stream. The flow rates and pressures of both streams may be separately adjusted/controlled. The superfusion stream flows across the flow conduit.

Figure 9:
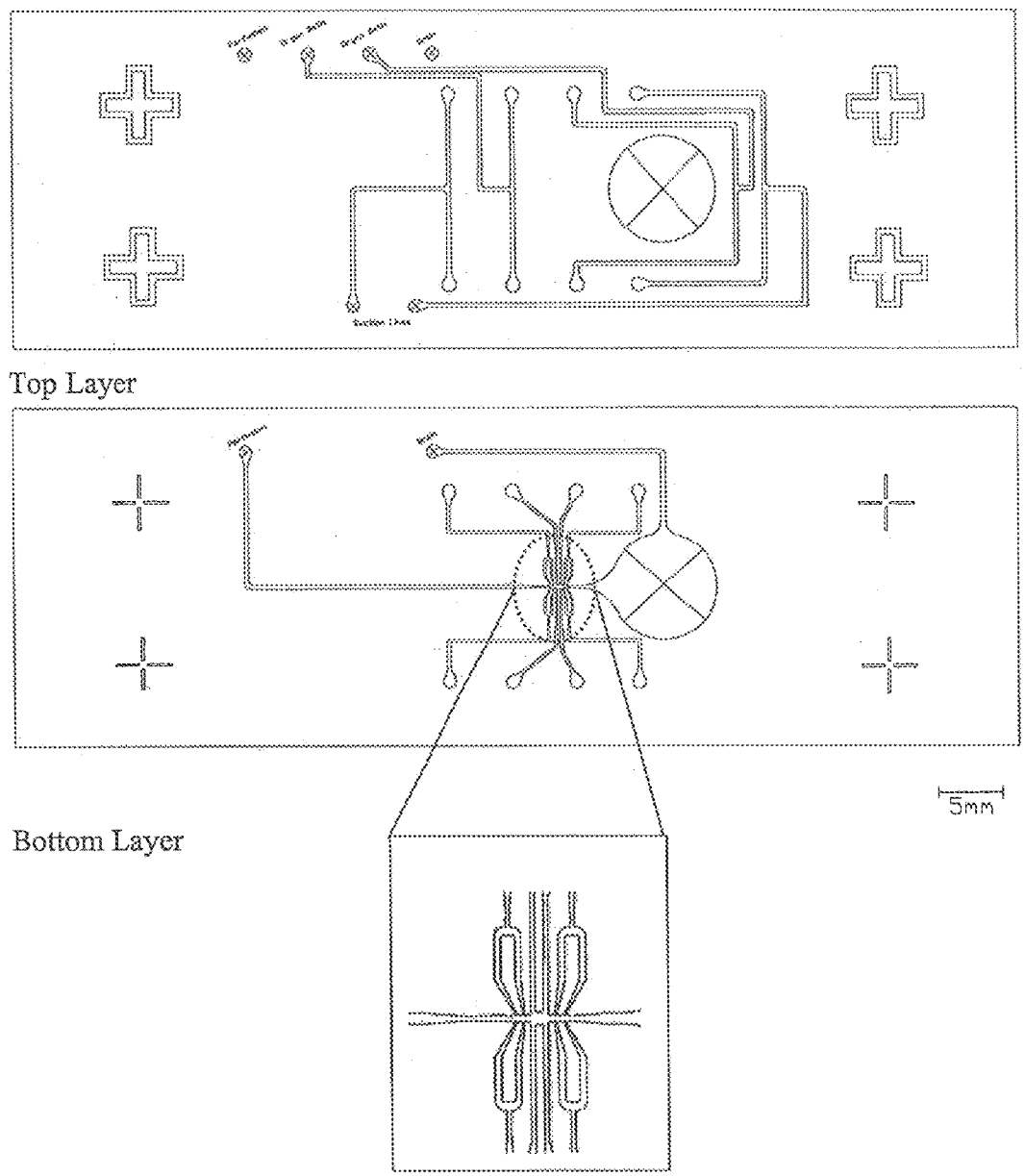

FIG. 9 is a schematic of an example device layout, showing a two-layer layout with a loading bath for loading a flow conduit. The upper image shows the top fluidic layer, and the bottom image shows the bottom fluidic layer of the device. The flow conduit enters the bottom layer of the device through a loading well into the main channel. The two fixation points at each end of the module are individually addressable. There is one culture channel for a superfusion stream and one inlet for a perfusion stream. The flow rates and pressures of both streams may be separately adjusted/controlled. The superfusion stream flow is first split before the two substreams flow along the flow conduit and are then guided from the device in separate outlets. In general, the superfusion stream may be split into two substreams, which may then be guided to enter left and right sides of the culture chamber simultaneously. This design may ensure a relatively rapid, gradient-free replacement of the contents in the culture chamber, and may also allow for stimulation of both sides of the flow conduit.

Figure 10:
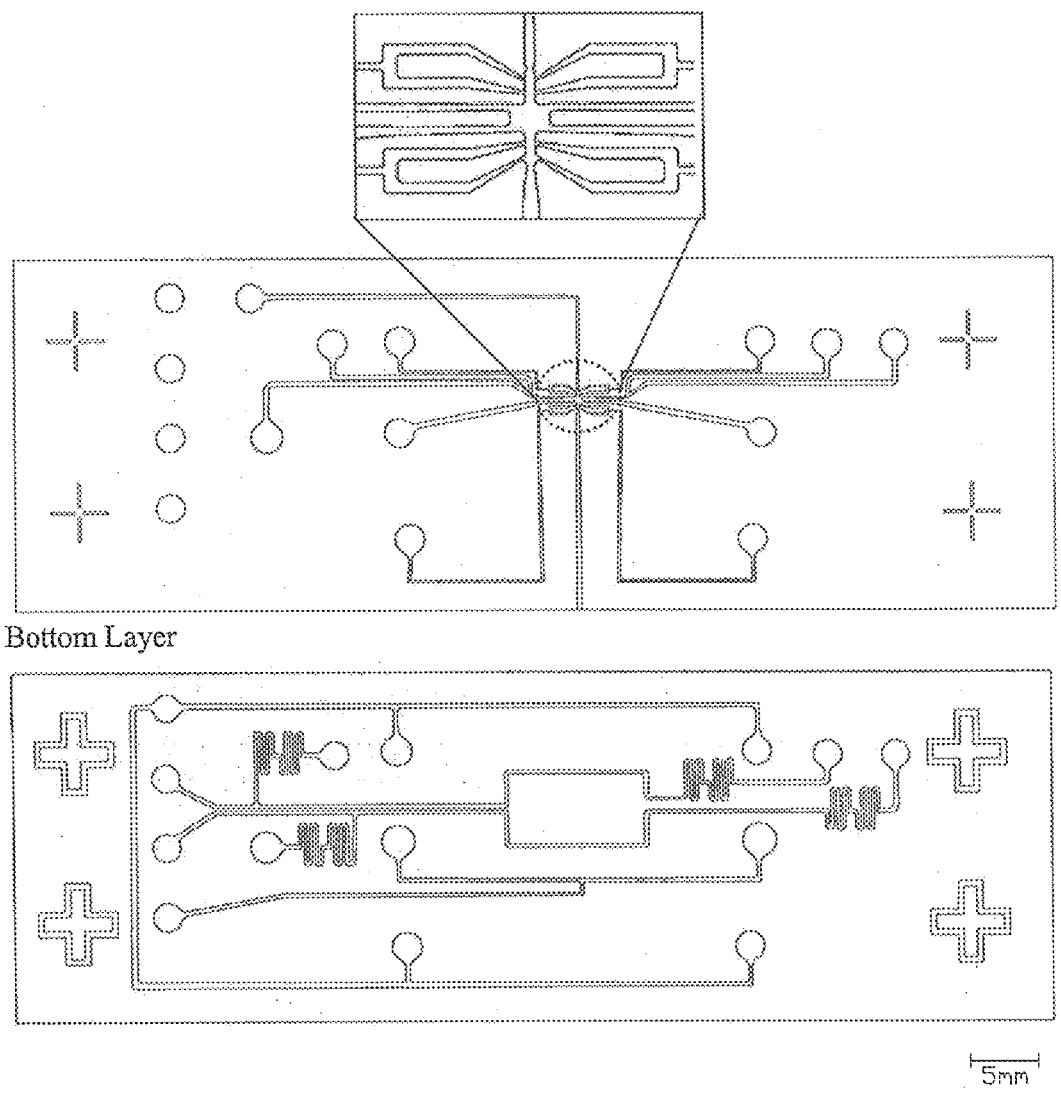

FIG. 10 is a schematic of an example device layout, showing a two-layer layout without a loading bath. The upper image shows the bottom fluidic layer, and the bottom image shows the top fluidic layer of the device. The flow conduit enters the bottom layer of the device at the bottom side through the main channel. The two fixation points at each end of the module are individually addressable. There is one culture channel for a superfusion stream and one inlet for a perfusion stream. The flow rates and pressures of both streams may be separately adjusted/controlled. The superfusion stream flows is first split before the two substreams flow along the flow conduit and are then guided from the device in separate outlets.

Figure 11:
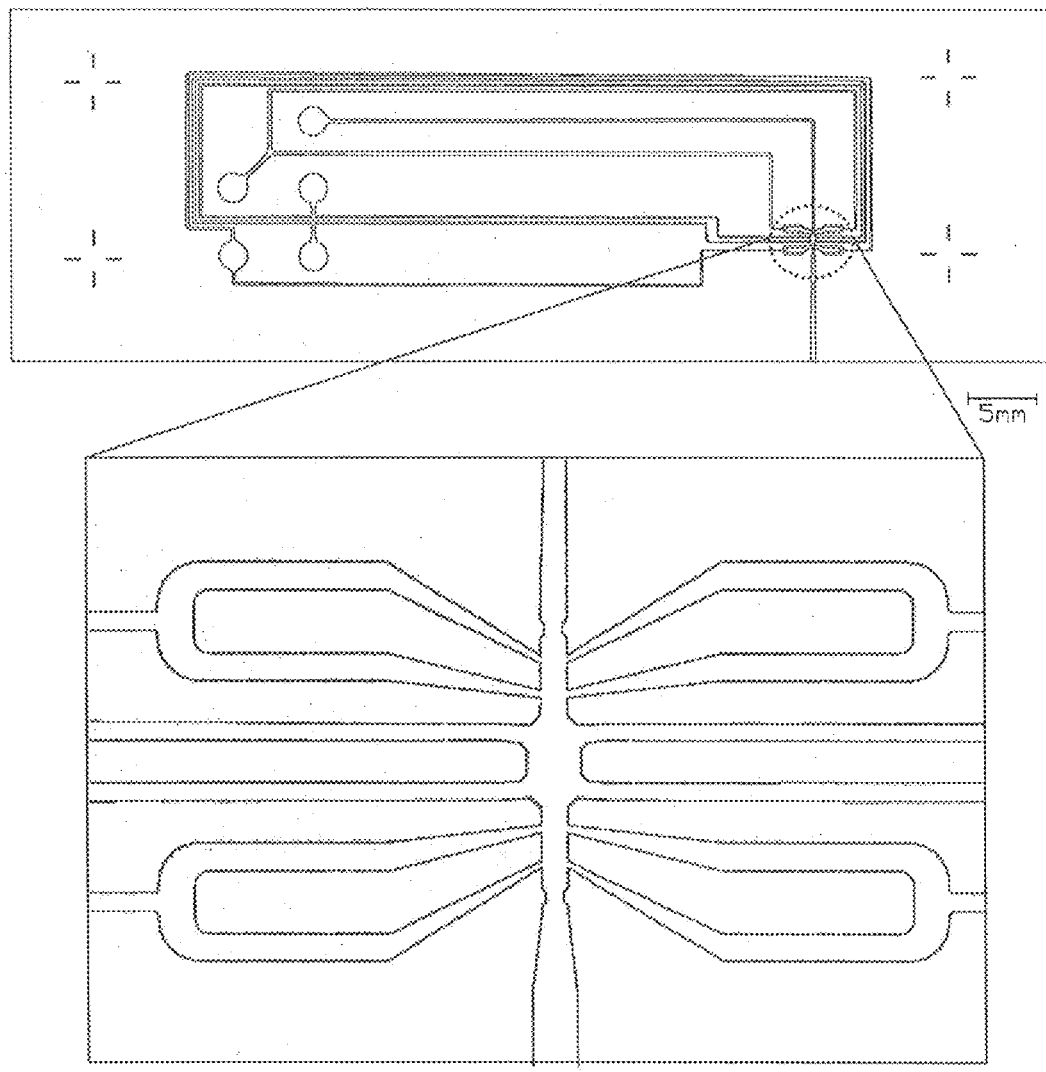

FIG. 11 is a schematic of an example device layout, showing a single-layer layout without a loading bath. The flow conduit enters the bottom layer of the device at the bottom side through the main channel. The two fixation points at each end of the module are individually addressable. There is one culture channel for a superfusion stream and one inlet for a perfusion stream. The flow rates and pressures of both streams may be separately adjusted/controlled. The superfusion stream flows is first split before the two substreams flow along the flow conduit and are then guided from the device in separate outlets.

Figure 12:
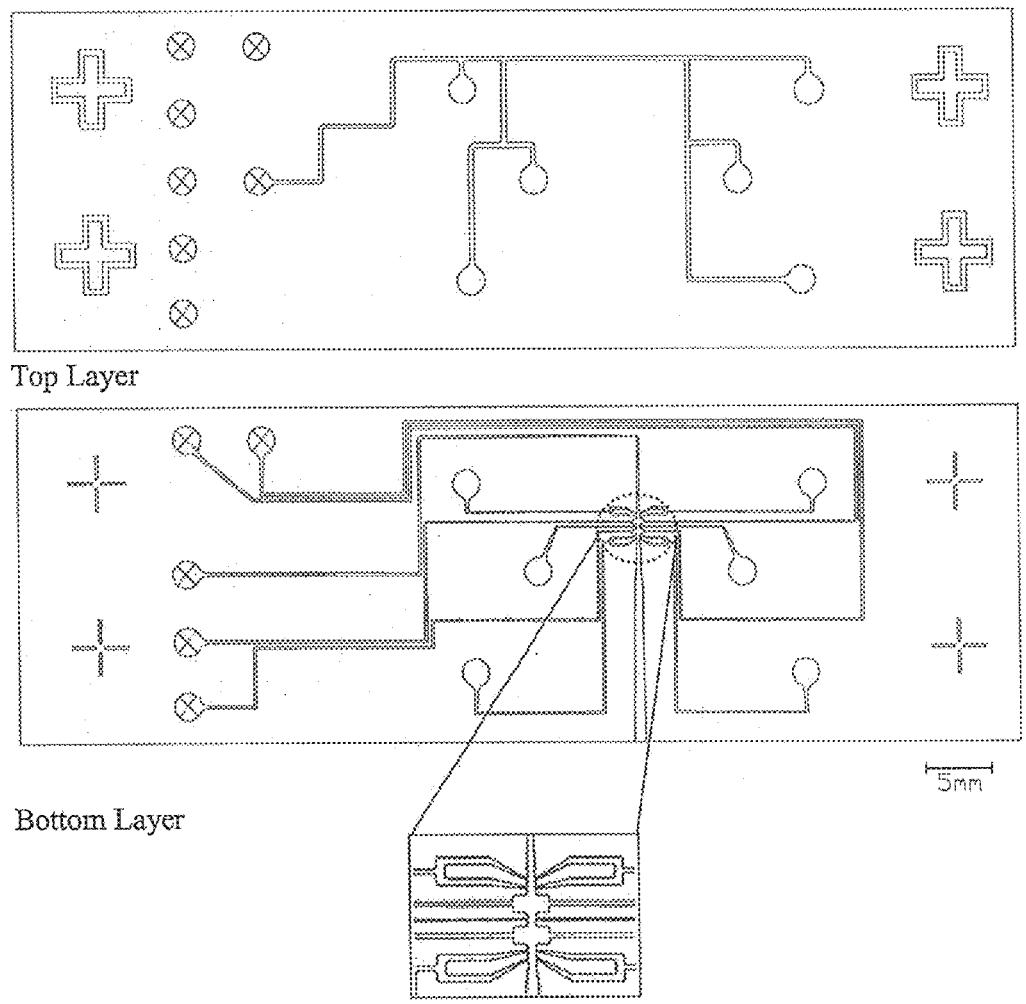

FIG. 12 is a schematic of an example device layout, showing a two-layer layout without a loading bath. The upper image shows the top fluidic layer, and the bottom image shows the bottom fluidic layer of the device. The flow conduit enters the bottom layer of the device at the bottom side through the main channel. The two fixation points at each end of the module are individually addressable. There is one culture channel for a superfusion stream and one inlet for a perfusion stream. The flow rates and pressures of both streams may be separately adjusted/controlled. The superfusion stream flows is first split before the two substreams flow along the flow conduit and are then guided from the device in separate outlets.

Figure 13:
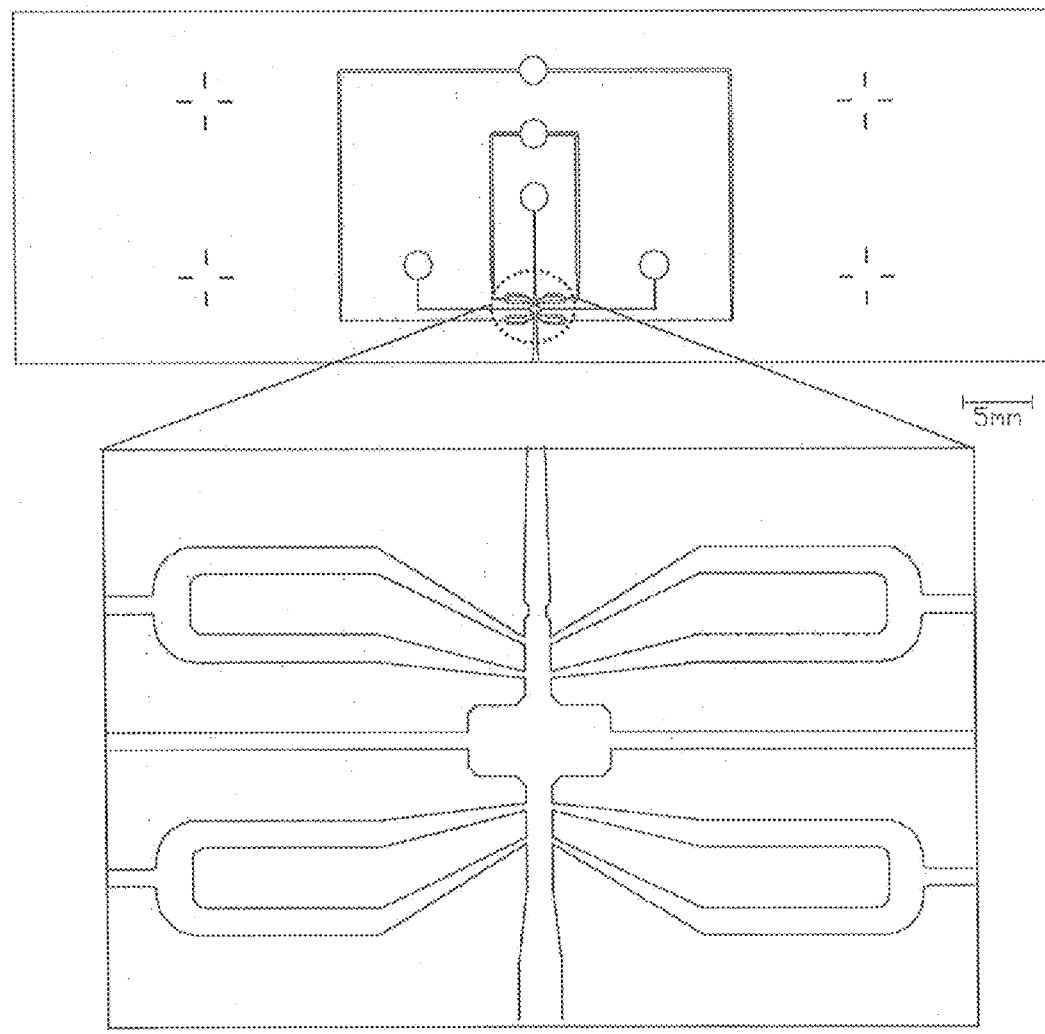

FIG. 13 is a schematic of an example device layout, showing a single-layer layout without a loading bath. The flow conduit enters the device at the bottom side through the main channel. The two fixation points at each end of the module are individually addressable. There is one culture channel for a superfusion stream and one inlet for a perfusion stream. The flow rates and pressures of both streams may be separately adjusted/controlled. The superfusion stream flows across the flow conduit and is then guided from the device in separate outlet.

Figure 14:
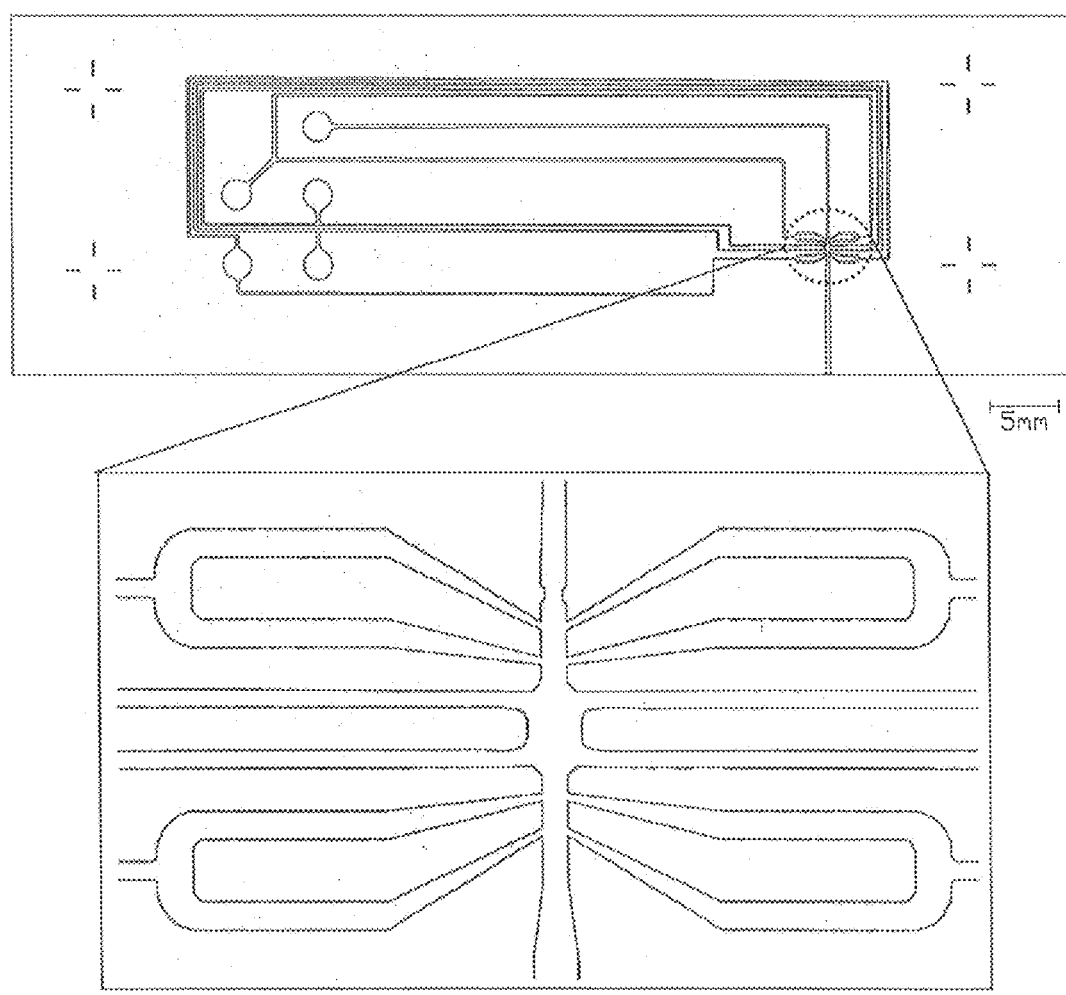

FIG. 14 is a schematic of an example device layout, showing a single-layer layout without a loading bath. The flow conduit enters the device at the bottom side through the main channel. The two fixation points at each end of the module are individually addressable. There is one culture channel for a superfusion stream and one inlet for a perfusion stream. The flow rates and pressures of both streams may be separately adjusted/controlled. The superfusion stream flows is first split before the two substreams flow along the flow conduit and are then guided from the device in separate outlets.

Figure 15:
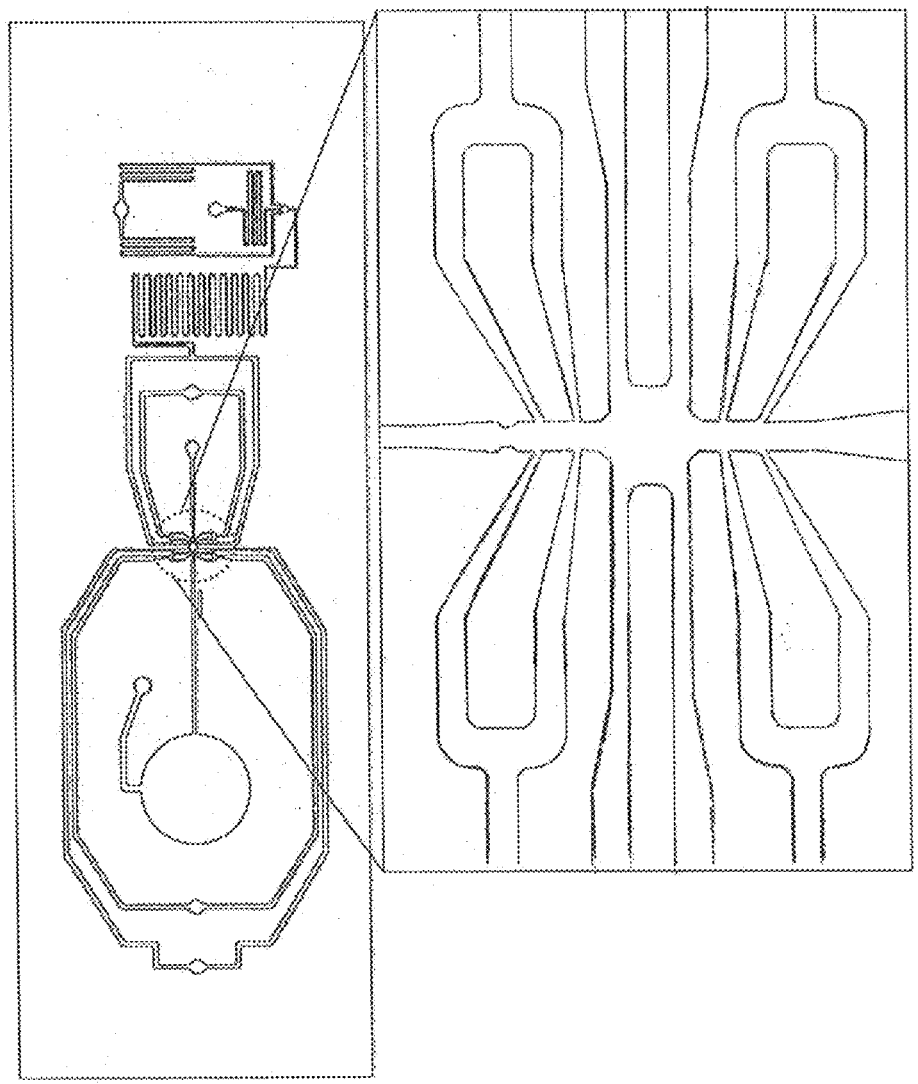

FIG. 15 is a schematic of an example device layout, showing a single-layer layout with a loading bath for loading a flow conduit. This example may be suitable for investigation of 150 μm conduits, such as a 150 μm blood vessel. The flow conduit enters the device through a loading well into the main channel. The two fixation points at each end of the module are individually addressable. There is one culture channel for a superfusion stream and one inlet for a perfusion stream. The flow rates and pressures of both streams may be separately adjusted/controlled. The two superfusion streams are first mixed by diffusion before they are split into two equal substreams that then flow along the flow outside of the conduit and are guided from the device in a joint outlet.

Figure 16:
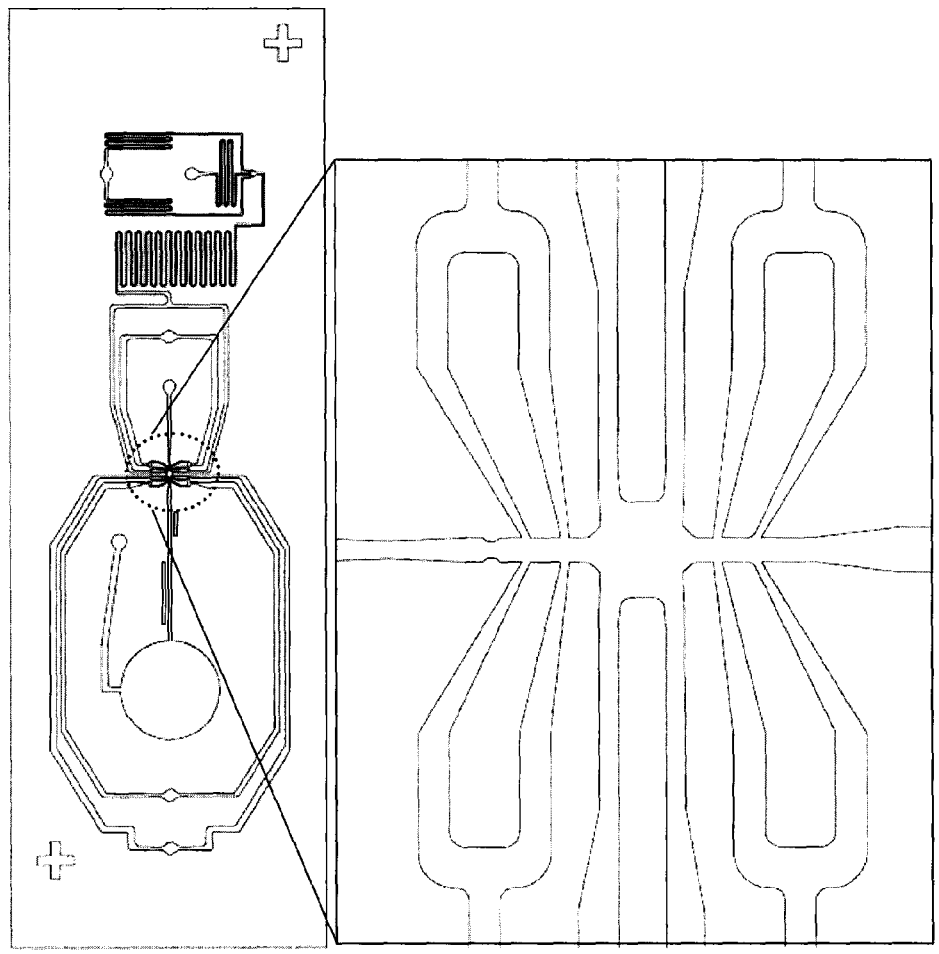

FIG. 16 is a schematic of an example device layout, showing a single-layer layout with a loading bath for loading a flow conduit. This example may be suitable for investigation of 120 μm conduits, such as a 120 μm blood vessel. The flow conduit enters the device through a loading well into the main channel. The two fixation points at each end of the module are individually addressable. There is one culture channel for a superfusion stream and one inlet for a perfusion stream. The flow rates and pressures of both streams may be separately adjusted/controlled. The two superfusion streams are first mixed by diffusion before they are split into two equal substreams that then flow along the flow outside of the conduit and are guided from the device in a joint outlet.

Figure 17:
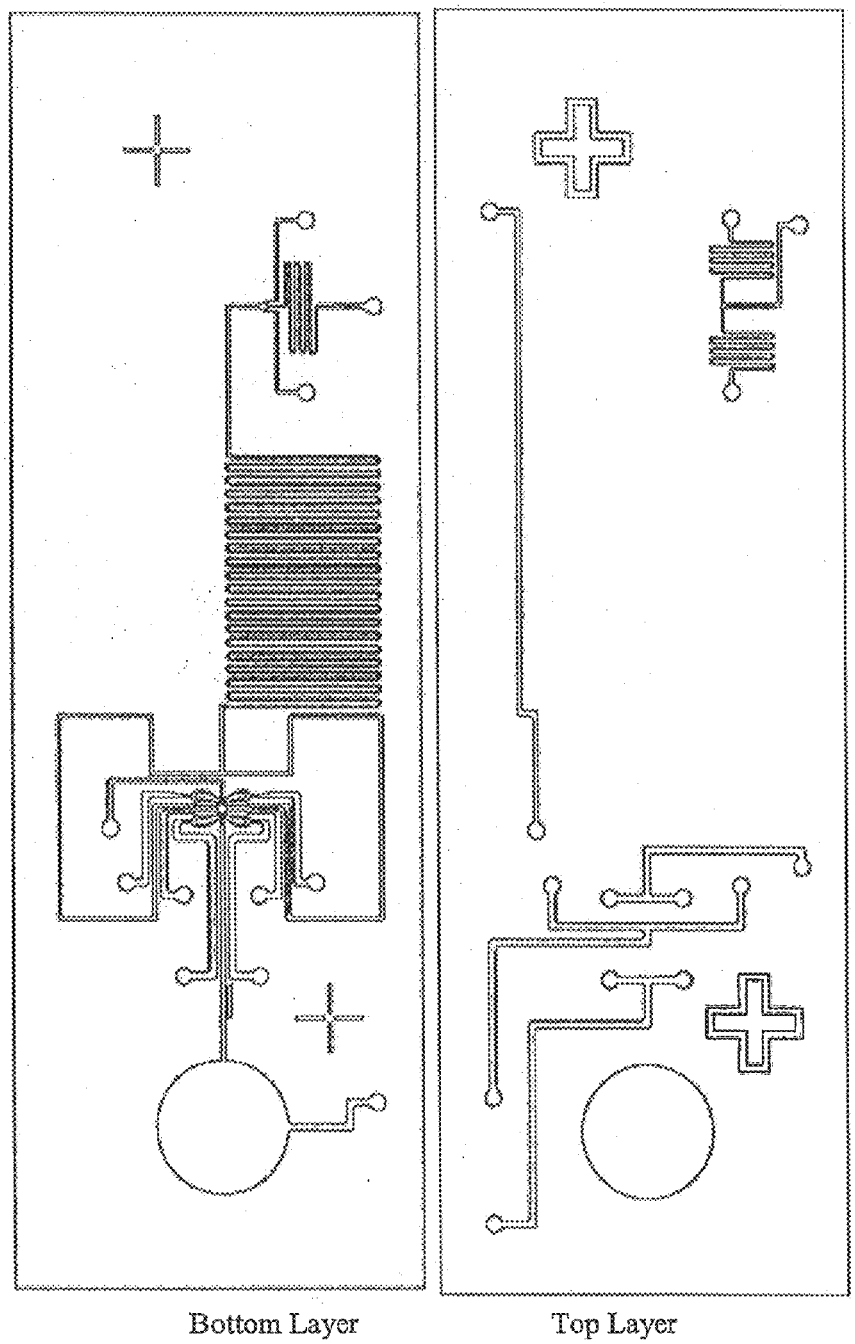

FIG. 17 is a schematic of an example device layout, showing a two-layer layout with a loading bath for loading a flow conduit. The left image shows the bottom fluidic layer, and the right image shows the top fluidic layer of the device. The flow conduit enters the device through a loading well into the main channel. The two fixation points at each end of the module are individually addressable. There are two culture channel for a superfusion stream and one inlet for a perfusion stream. All individual flow rates of the superfusion/perfusion streams and the pressure in the resulting total superfusion stream and the perfusion stream may be separately adjusted/controlled. The two superfusion streams are first mixed by diffusion before they are split into two equal substreams that then flow along the flow outside of the conduit and are guided from the device in a joint outlet.

Figure 18:
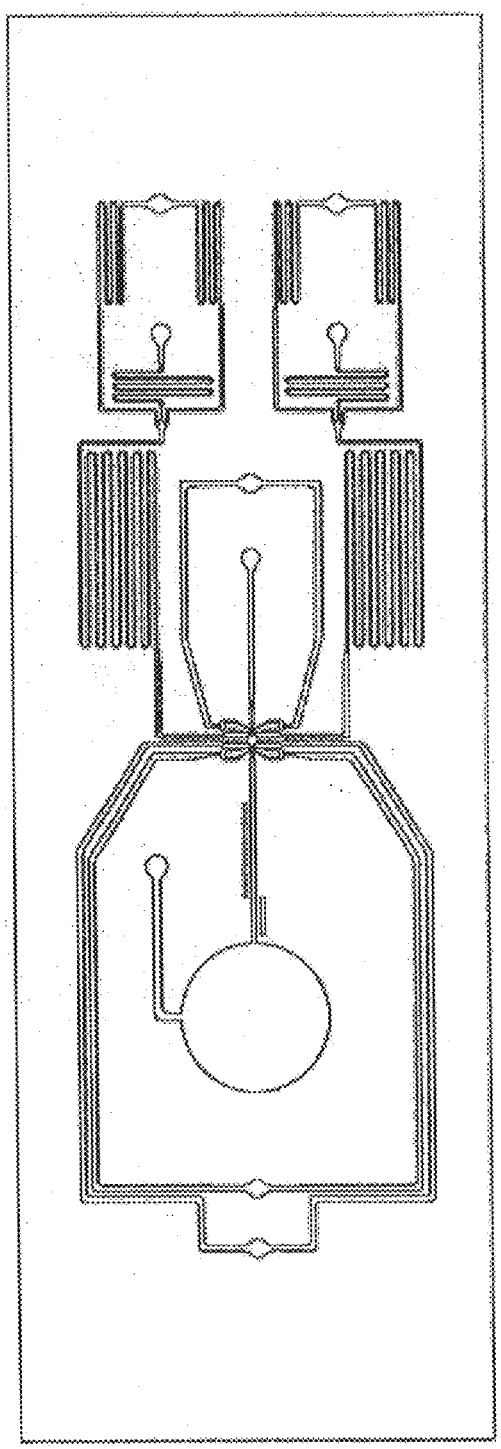

FIG. 18 is a schematic of an example device layout, showing a single-layer layout with a loading bath for loading a flow conduit. In this example, there is one common perfusion line and two separate superfusion lines to the left and right sides of the culture chamber. The flow conduit enters the device through a loading well into the main channel. The two fixation points at each end of the module are individually addressable. All individual flow rates of the superfusion/perfusion streams and the pressure in the resulting total superfusion stream and the perfusion stream may be separately adjusted/controlled. On each side along the axis of the flow conduit, two superfusion streams, which may be different, are first mixed by diffusion before they flow at opposite sides along the outside of the conduit.

Figure 19:
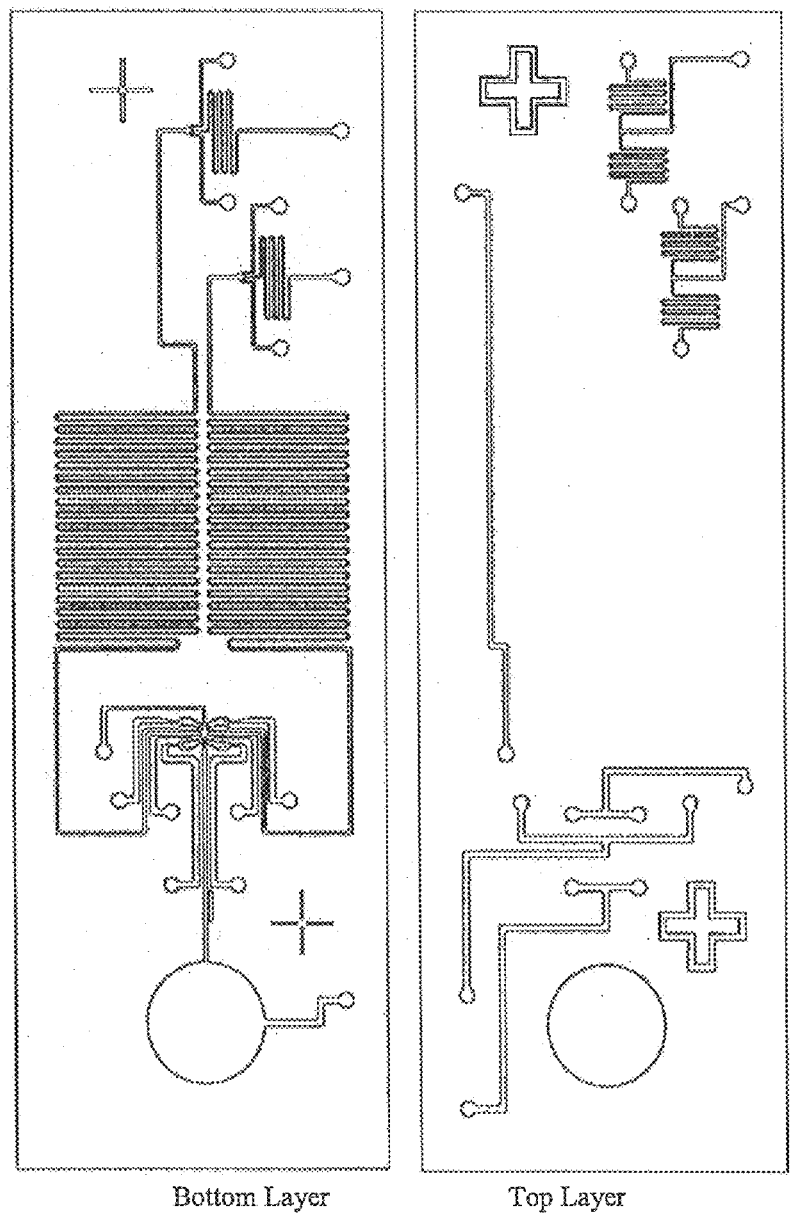

FIG. 19 is a schematic of an example device layout, showing a two-layer layout with a loading bath for loading a flow conduit. In this example, there is a common perfusion line and two separate superfusion lines to the left and right sides of the culture chamber. The left image shows the bottom fluidic layer, and the right image shows the top fluidic layer of the device. The flow conduit enters the device through a loading well into the main channel that is contained in the bottom layer. The two fixation points at each end of the module are individually addressable. All individual flow rates of the superfusion/perfusion streams and the pressure in the resulting total superfusion stream and the perfusion stream may be separately adjusted/controlled. On each side along the axis of the flow conduit, two superfusion streams, which may be different, are first mixed by diffusion before they flow at opposite sides along the outside of the conduit.

Figure 20:
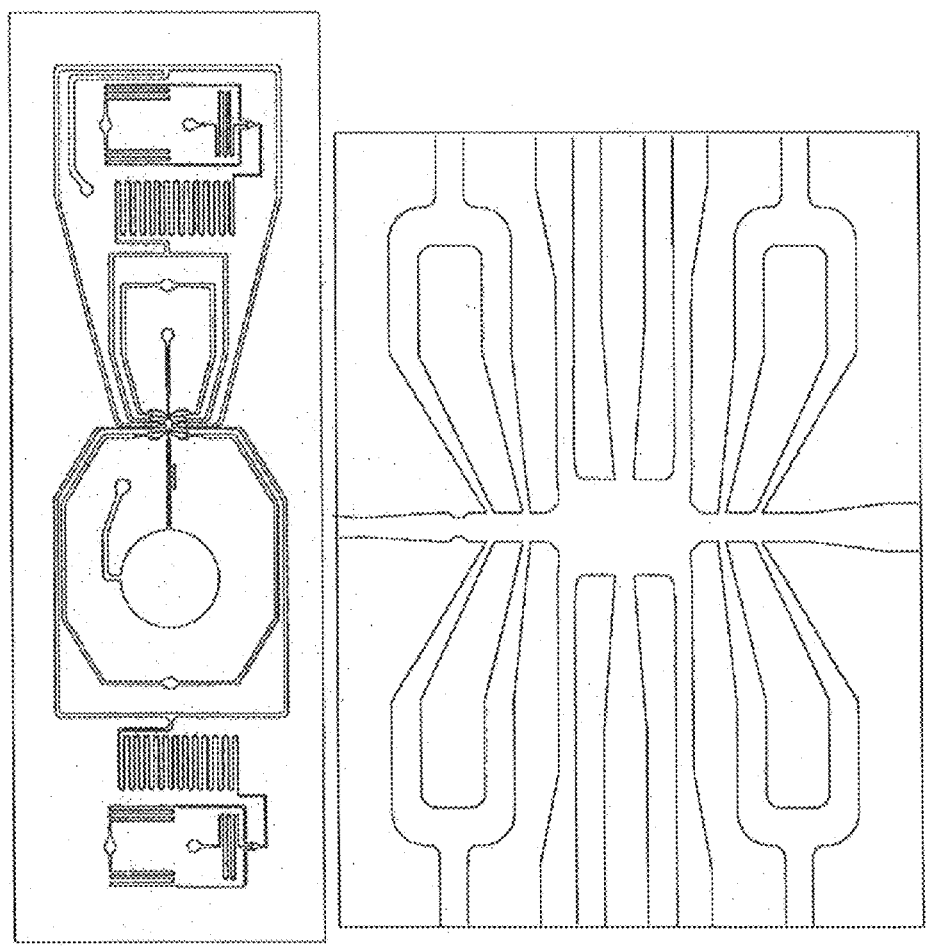

FIG. 20 is a schematic of an example device layout, showing a single-layer layout with a loading bath for loading a flow conduit. In this example, there is a common perfusion line. This layout may allow for a step change in the concentration of the superfusing stream applied in the axial direction. The flow conduit enters the device through a loading well into the main channel. The two fixation points at each end of the module are individually addressable. All individual flow rates of the superfusion/perfusion streams and the pressure in the resulting total superfusion stream and the perfusion stream may be separately adjusted/controlled. Two superfusion streams, which may be different, are first mixed by diffusion before they are subjected to different sections along the axis of the flow conduit. For viable flow conduits, this design may allow the creation of a microenvironment that may not be found in the conduits physiological environment.

Figure 21:
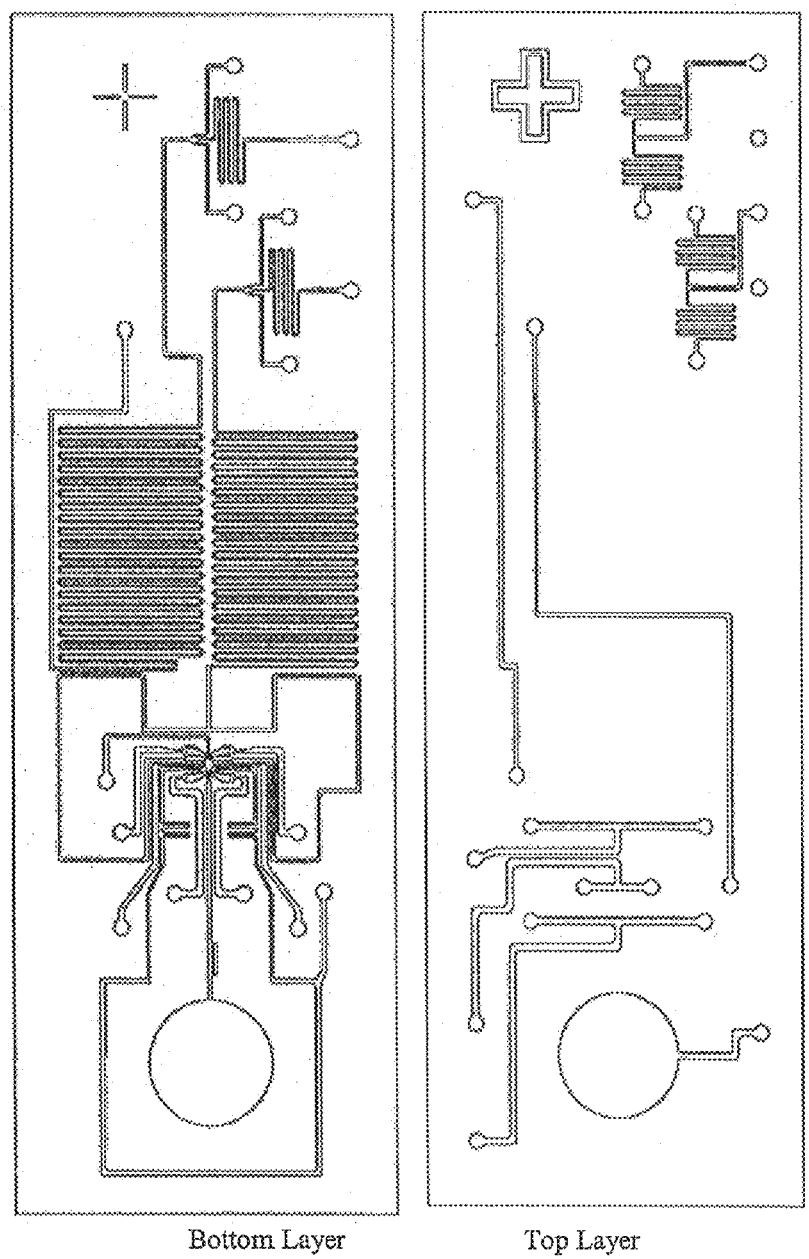

FIG. 21 is a schematic of an example device layout, showing a two-layer layout with a loading bath for loading a flow conduit. In this example, there is a common perfusion line. This layout may allow for a step change in the concentration of the superfusing stream applied in the axial direction. The left image shows the bottom fluidic layer, and the right image shows the top fluidic layer of the device. The flow conduit enters the device through a loading well into the main channel that is located in the bottom layer. The two fixation points at each end of the module are individually addressable. All individual flow rates of the superfusion/perfusion streams and the pressure in the resulting total superfusion stream and the perfusion stream may be separately adjusted/controlled. Two superfusion streams, which may be different, are first mixed by diffusion before they are subjected to different sections along the axis of the flow conduit. For viable flow conduits, this design may allow the creation of a microenvironment that may not be found in the conduits physiological environment.

Figure 22:
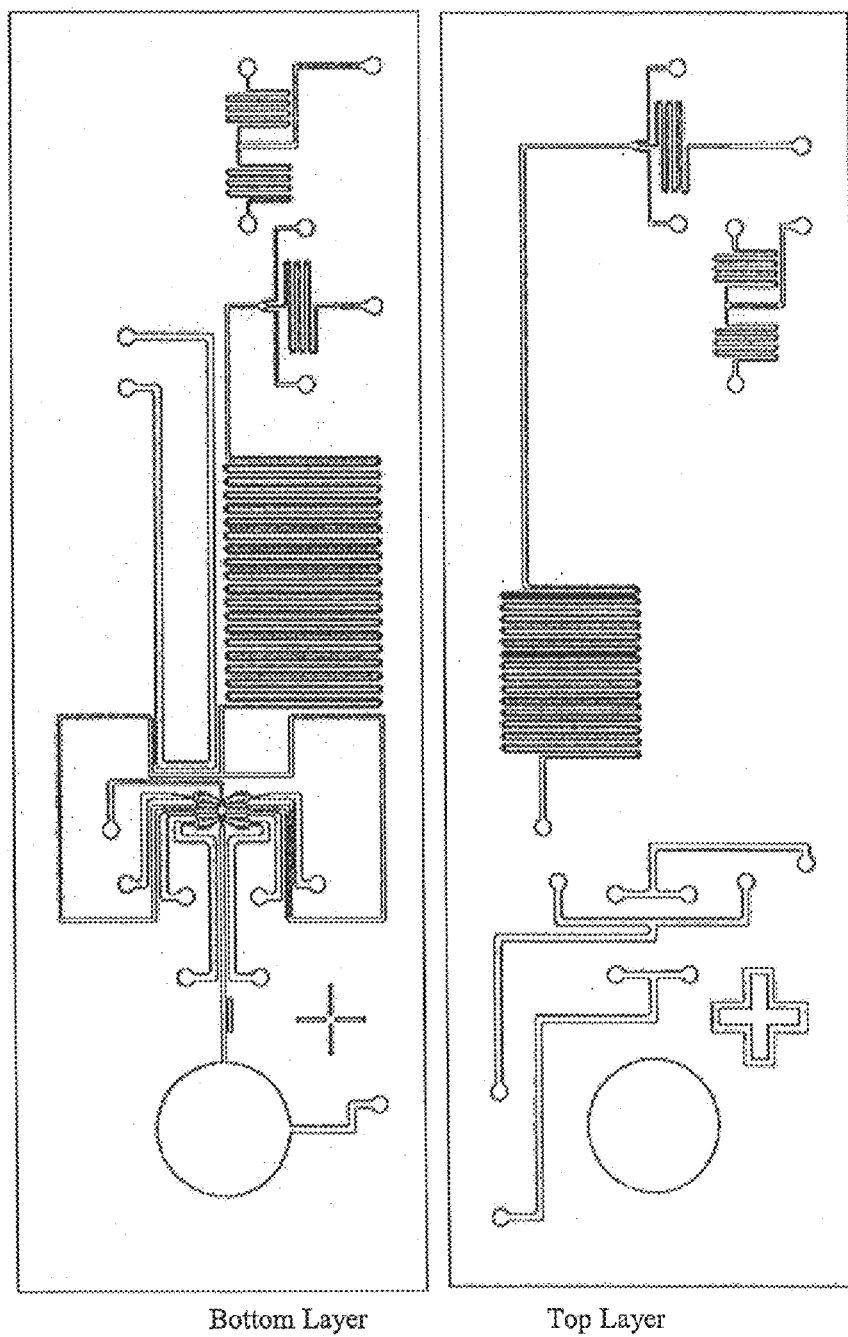

FIG. 22 is a schematic of an example device layout, showing a two-layer layout with a loading bath for loading a flow conduit. In this example, there is a common perfusion line. This layout may allow the concentration in the superfusion stream to be varied over time by diffusive mixing of two sub-streams. The left image shows the bottom fluidic layer, and the right image shows the top fluidic layer of the device. The flow conduit enters the device through a loading well into the main channel that is located in the bottom layer. The two fixation points at each end of the module are individually addressable. All individual flow rates of the superfusion/perfusion streams and the pressure in the resulting total superfusion stream and the perfusion stream may be separately adjusted/controlled. Two separate superfusion streams are first mixed by diffusion before they meet the outside of the flow conduit. Two separate perfusion streams are first mixed by diffusion before they meet the inside of the flow conduit.

Figure 23:
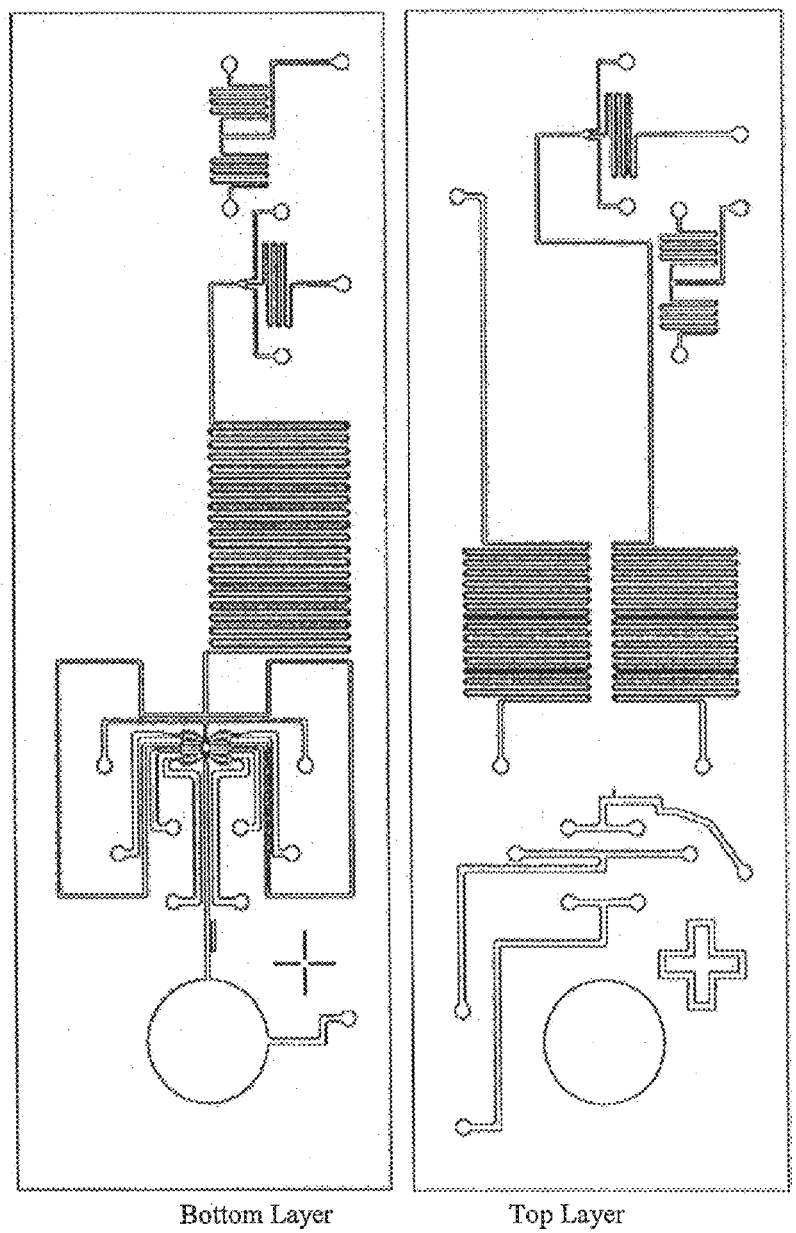

FIG. 23 is a schematic of an example device layout, showing a two-layer layout with a loading bath for loading a flow conduit. In this example, there are two perfusion lines, allowing two perfusion streams to contact each other without mixing. This layout may allow the concentration in the superfusion stream to be varied over time by diffusive mixing of two sub-streams. The left image shows the bottom fluidic layer, and the right image shows the top fluidic layer of the device. The flow conduit enters the device through a loading well into the main channel that is located in the bottom layer. The two fixation points at each end of the module are individually addressable. All individual flow rates of the superfusion/perfusion streams and the pressure in the resulting total superfusion stream and the perfusion stream may be separately adjusted/controlled. Two separate superfusion streams are first mixed by diffusion before they meet the outside of the flow conduit. Two separate perfusion streams meet the inside of the flow conduit at opposite sides, with minimum diffusive mixing. For viable flow conduits, this design may allow for the creation of a microenvironment that may not be found in the conduits physiological environment.

Figure 24:
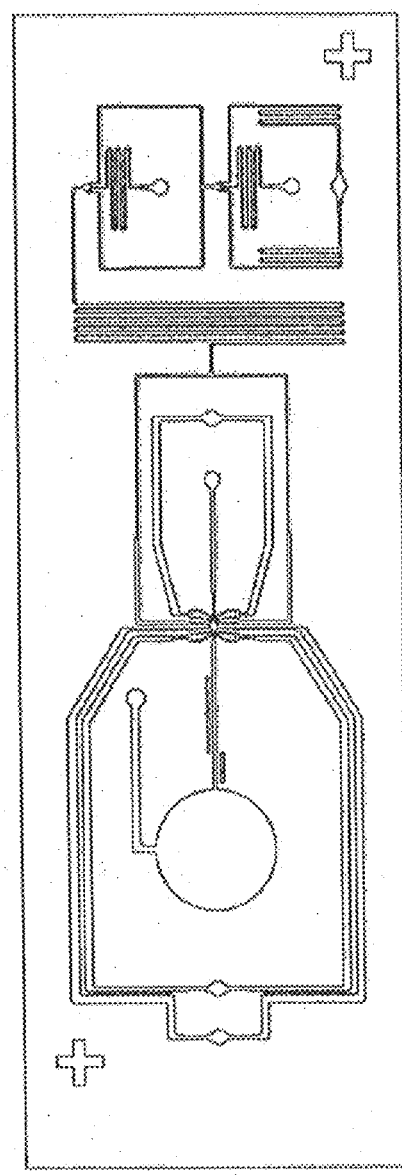

FIG. 24 is a schematic of an example device layout, showing a single-layer layout with a loading bath for loading a flow conduit. In this example, there is a common perfusion line. There may be three different superfusing lines allowing different superfusing streams that may be mixed by diffusion. The flow conduit enters the device through a loading well into the main channel. The two fixation points at each end of the module are individually addressable. All individual flow rates of the superfusion/perfusion streams and the pressure in the resulting total superfusion stream and the perfusion stream may be separately adjusted/controlled. Three separate superfusion streams are first mixed by diffusion before they meet the outside of the flow conduit.

Multi-Module Designs

In addition to the single-module design, there may be a plurality of modules provided on a single device. The modules may be formed in the base in a series arrangement, a parallel arrangement, a network arrangement, or other multiplex arrangements.

Examples of Modules in Series

Two or more modules may be arranged in series on the device. Aside from having a common main channel and common loading inlet, each module may be functionally similar to the single module described above. In some example embodiments, the modules may be in series without sharing a common main channel or common loading inlet. Flow conduits may be serially loaded into each module and fixed using fixation lines at each module. Each module may share the same perfusion pump, superfusion pump and/or low pressure source, such that conduits fixed in each modules may be essentially subjected to the same conditions. Alternatively, conduits in each of the modules may be subjected to different conditions, such as by using separate perfusion pumps which may allow, for example, perfusing a compound to the culture chamber of one module, but not to any other.

Loading, fixation, investigation, and unloading of the flow conduits may be the same as discussed above. Typically, the flow conduits may be loaded in sequence, with the first flow conduit being loaded and fixed in the module farthest from the loading inlet before the next flow conduit is loaded into a closer module.

Figure 25:
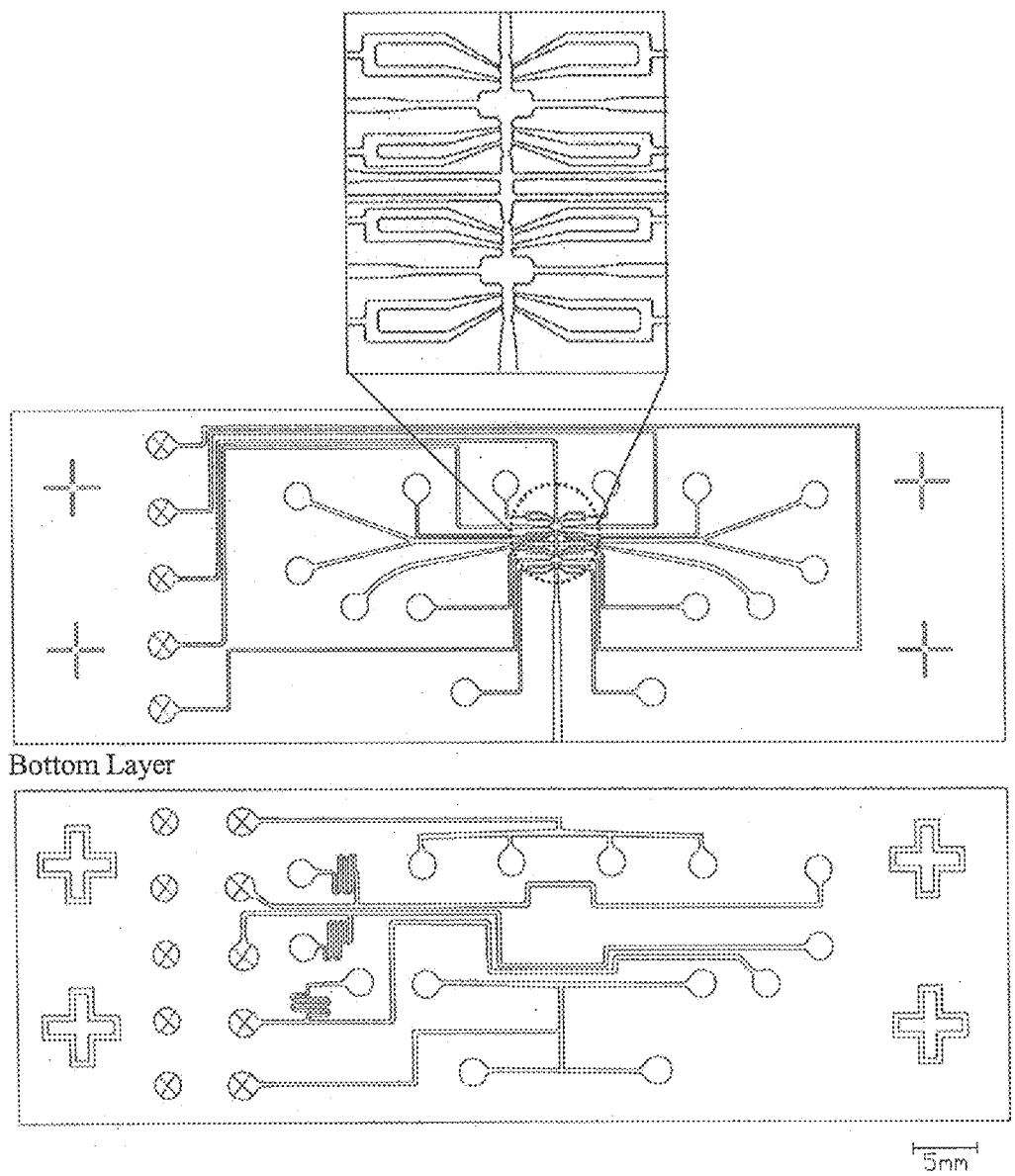
FIGS. 25-27 illustrate example embodiments of a device for investigation of a flow conduit having a series design.

FIG. 25 is a schematic of an example device layout, showing a two-layer layout without a loading bath. There are two modules in series. Either two short flow conduits or one long flow conduit that extends over all fixation locations may enter the device through the main channel located in the bottom layer. In this example, there is a common perfusion line, individual fixation lines and two separate superfusing lines. Individual flow conduit or individual sections of the same flow conduit (e.g., in the case of a long enough flow conduit) may be superfused across its/their axis.

Figure 26:
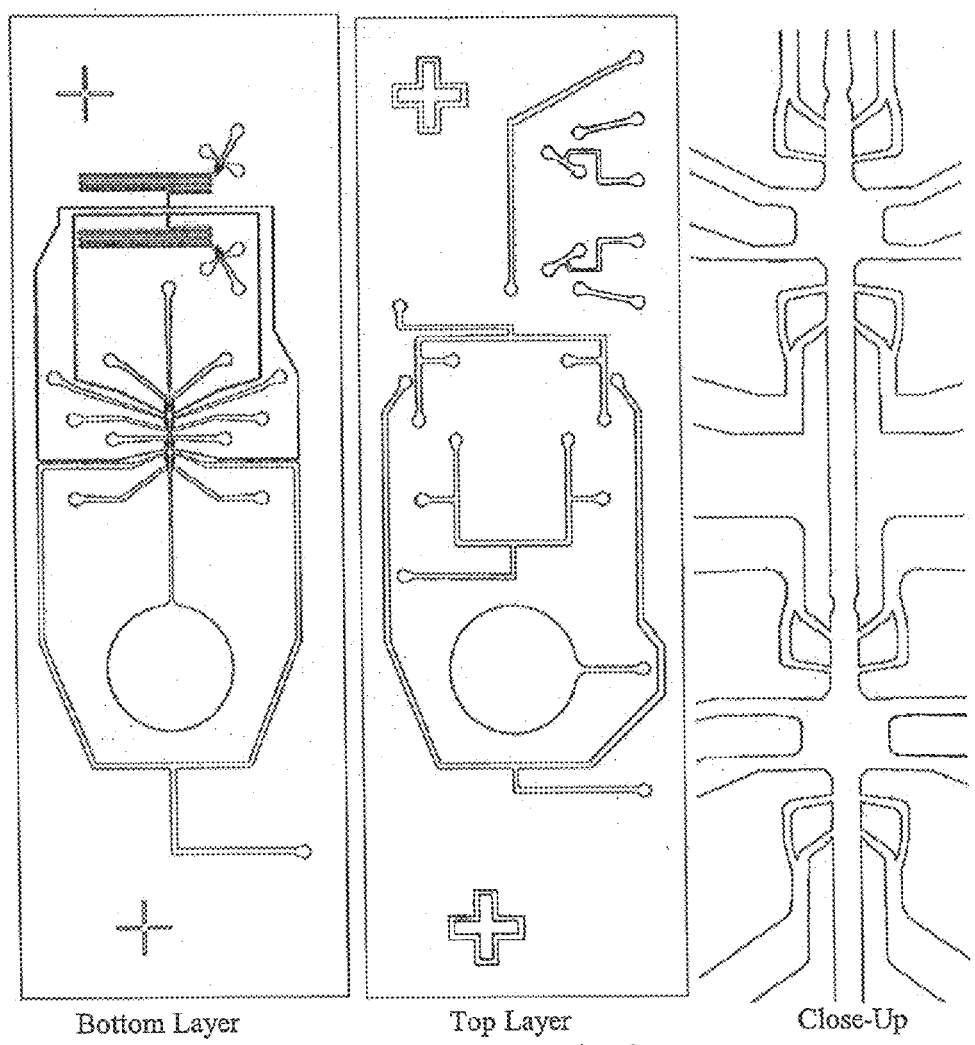

FIG. 26 is a schematic of an example device layout, showing a two-layer layout with a loading bath for loading a flow conduit. There are two modules in series. Either two short flow conduits or one long flow conduit that extends over all fixation locations may enter the device through the loading bath into the main channel located in the bottom layer. In this example, there is a common perfusion line, individual fixation lines and two separate superfusing lines. Individual flow conduit or individual sections of the same flow conduit (e.g., in the case of a long enough flow conduit) may be superfused across its/their axis.

Figure 27:
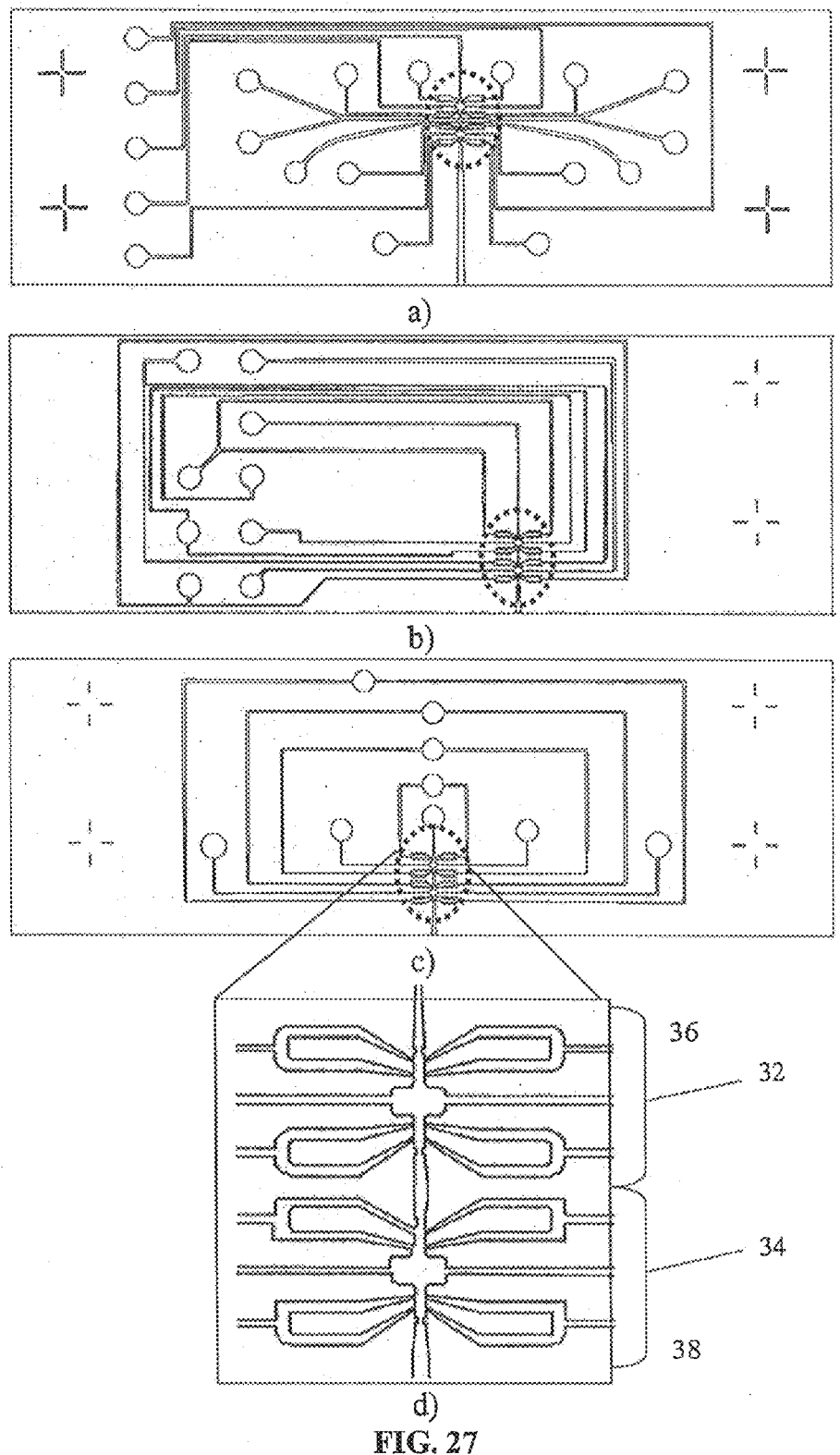

FIG. 27 shows different schematics of example device layouts, having single-layer layouts with a loading bath for loading a flow conduit. These example layouts have two modules in series. Either two short flow conduits or one long flow conduit that extends over all fixation locations enter the device through the main channel located in the bottom layer. In this example, there is a common perfusion line, individual fixation lines and two separate superfusing lines. Individual flow conduit or individual sections of the same flow conduit (e.g., in the case of a long enough flow conduit) may be superfused across its/their axis.

Although these examples show only two modules series, it would be clear to a person skilled in the art that the device could be designed to have more modules in series. In some examples, the modules in series may share a common culture chamber. That is, a common longer culture chamber may be used with more than two fixation points for fixing multiple flow conduits or multiple portions of a flow conduit along the length of the culture chamber.

A series design of this device may be useful, for example in performing bioassays, and for studying healing processes. For example, in a bioassay, pharmaceutical agents may be administered to an upstream artery only (i.e., one closer to the loading inlet) and the effects on a downstream artery (i.e., one farther from the loading inlet) may be observed. For studying healing or joining of arteries, two or more separate arteries may be loaded in sequential modules and fixed with a small gap between adjacent ends.

Growth and joining of the separate artery ends may be observed over time, as well as the effectiveness of various agents in promoting such growth.

Examples of Modules in Parallel

Two or more modules may be arranged side-by-side in parallel on a single device. The modules may have similar connections and may be functionally similar to the single module described above. The modules may share the same perfusion pump, superfusion pump and/or low pressure source, such that flow conduits fixed in each module may be essentially subjected to the same conditions. Alternatively, conduits in each of the modules may be subjected to different conditions, such as by using separate perfusion pumps, which may allow, for example, perfusing a compound to the culture chamber of one module, but not to any other module on the device. The modules may share a common culture chamber and culture channel. That is, the culture chambers and culture channels of each of the modules may be connected together. Loading, fixation, investigation, and unloading of the flow conduits may be the same as discussed above.

Figure 28:
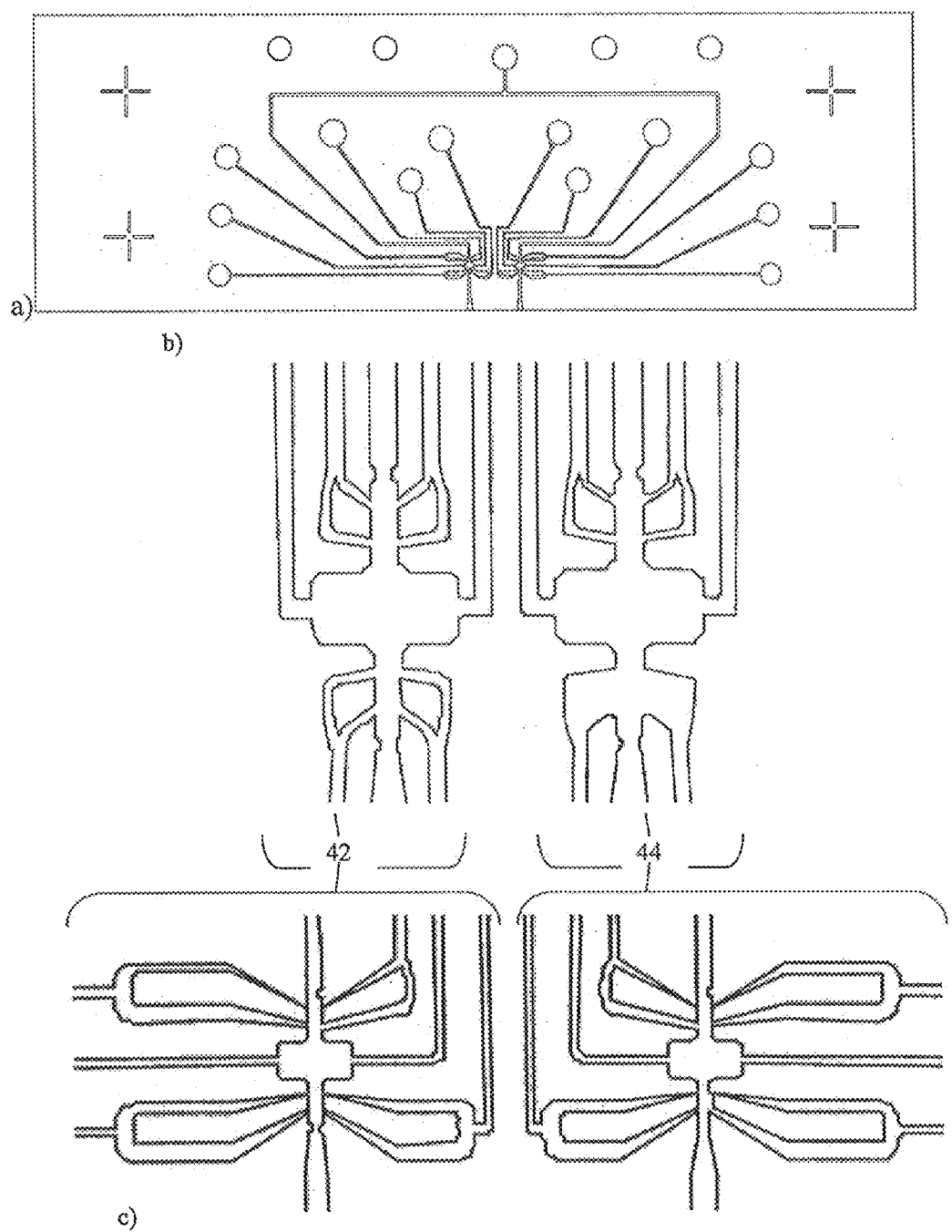
FIGS. 28-29 illustrate example embodiments of a device for investigation of a flow conduit having a parallel design.

FIG. 28 shows different schematics of example device layouts, having single-layer layouts without a loading bath for loading a flow conduit. These example layouts have two modules in parallel. Two flow conduits may enter the device through individual main channels. In this example, there is a common perfusion line, individual fixation lines and separate superfusing lines. The two flow conduits fixed in each module may be superfused with separate streams across their axis.

Figure 29:
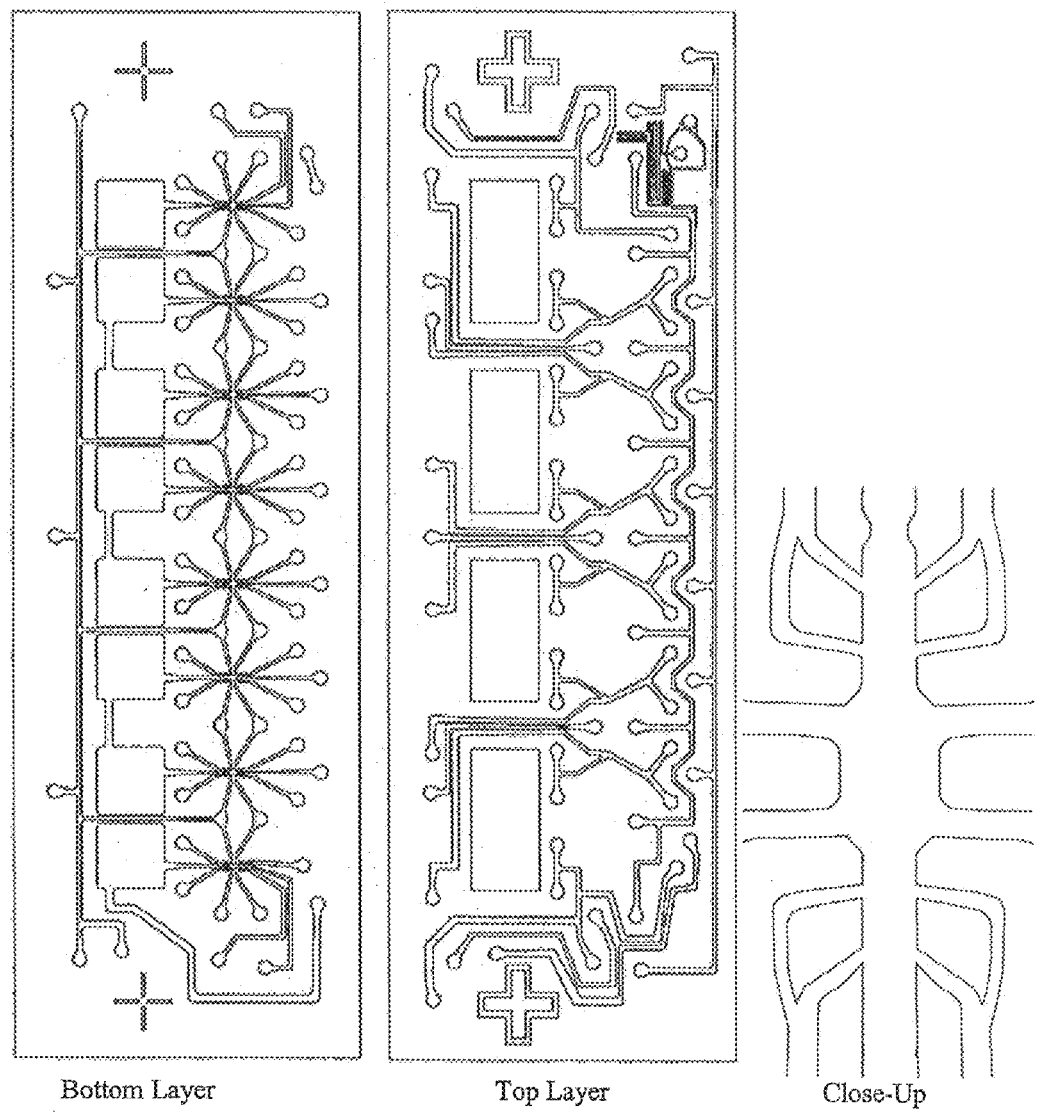

FIG. 29 shows different schematics of example device layouts, having two-layer layouts with separate interconnected loading baths for loading several parallel flow conduits. The flow conduits may be loaded through individual main channels that are located in the bottom layer. These example layouts each have eight modules in parallel.

Although only two or eight modules are shown in parallel, it would be clear to a person skilled in the art that the device could be designed to have different numbers of modules in parallel.

A parallel design of this device may be useful in ensuring that the flow conduits being investigated are subjected to the same conditions at essentially the same time. For example, it might be desirable to obtain results from a large number of arteries under the same conditions (e.g., culture medium, flow conditions) at essentially the same time for statistical purposes. Fixing all the arteries in the same device in a parallel arrangement may allow all the arteries to be tested together at the same time, under the same conditions. A parallel arrangement may also be useful in automating testing procedures, as the parallel flow conduits may be stepped through one-by-one in progression (e.g., in an automated analyzer) simply by advancing the device module-by-module.

In addition to the series and parallel arrangements described above, other multiplex arrangements are possible. For example, the series and parallel arrangements may be combined to obtain an array arrangement of modules on a single device. The modules may also be arranged in a branching network, circular network, or any other desired arrangement. In all cases, some or all modules may have separate culture chambers or they may share culture chambers and culture channels. Some or all modules may have individual perfusion pumps, superfusion pumps, low pressure sources, and other inlets and outlets, or these may be shared among some or all modules. The modules may all employ the same fixation method (e.g., reversible or irreversible), or they may use different fixation methods.

Examples with Integrated Optical Fiber

Figure 30:
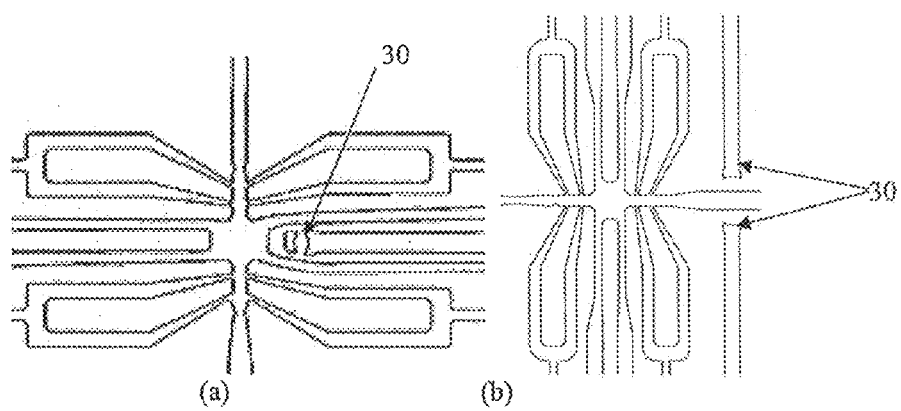
FIG. 30 illustrates example embodiments of a device for investigation of a flow conduit having an integrated optical fiber.

FIG. 30 illustrates example embodiments of the device having an integrated optical fiber. Here, the example has a single-layer layout with a loading bath. Single- or multimode optical fibers may be inserted through a straight channel that connects, for example, to a corner of the device. Small lenses may be embedded in the module (e.g., as described in "PDMS 2D optical lens integrated with microfluidic channels: principle and characterization" Camou S, Fujita H, Fujii T, Lab on a Chip 3 (1), 40-45 2003) to focus the light emitted by the fiber to a location within the main channel.

This design may allow a laser light to be guided towards a fixed flow conduit via the optical fiber. For example, such a setup may be useful in angiogenesis studies to set precisely defined injuries as a prerequisite or initiator for subsequent growth of endothelial cells out of the lumen of a vessel. In this example, a single- or multi-mode optical fiber or waveguide 30 may be embedded in the device to guide light from a laser into the device. Pulse lasers (e.g., pulsed Nd:YAG or ultrafast pulse lasers) or continuous-wave lasers are possible laser sources. Light leaving the optical fiber or waveguide 30 may be focused by a lens in the device towards the vascular wall where it causes precisely defined injuries.

Applications

This device may be provided on a chip or microdevice, for example as a microfluidic chip or a lab-on-a-chip. This may allow for miniaturization and scaling of many assays and tests, allowing for high-throughput. For example, the procedure described in WO 2003/078606 (Bolz) may be carried out using this device, and may be relatively easier and more efficiently performed, even by relatively less-trained technicians.

In general, the device may be used for investigating a flow conduit. The flow conduit may be loaded into the main channel and fixed in place with at least a portion of the conduit in the culture chamber. A physiological solution, which may contain a compound of interest such as a biological factor, may be perfused or superfused over the conduit. The flow conduit may then be monitored to investigate any responses.

Any of the methods discussed above may be used to analyze or monitor the flow conduit, including bright field or fluorescence microscopy techniques, fluorescence intensity and fluorescence lifetime-based imaging, optical spectroscopy, on-chip lysis and mass spectrometry. Monitoring may also be done by taking diameter measurements, for example using an integrated optical technique, such as a laser-optical technique.

Research of Blood Vessels

The device may be combined with imaging techniques such as transient $Ca^{2+}$ imaging to obtain time-resolved recordings of the contractile state of a flow conduit, such as the artery, and $Ca^{2+}$ responses. The device may include lysis capabilities as described above, and may be designed to interface to a mass spectrometer.

Standard characterization of blood vessels includes measurements of the artery tone and/or diameter that are performed at inverted bright field and fluorescence microscopes. This device may be combined with various types of bright field or fluorescence imaging, including $Ca^{2+}$ imaging to obtain time-resolved recordings of the contractile state of the artery and $Ca^{2+}$ responses. Lysis capabilities may be included as well as automated interfaces to electrophoresis, fluorescence spectroscopy, and mass spectrometry.

One research interest is to map intracellular processes in vascular smooth muscle cells of the vascular wall. However, primary smooth muscle cells in culture tend to de-differentiate within hours from a contractile phenotype to a synthetic phenotype. One of the most prominent changes that are observed is the reorganization of the actin-based cytoskeleton. Thus, it may be desirable to use cellular models where this de-differentiation effect does not occur. Also desirable are advanced experimental systems that will allow the study of transport processes in intact tissues (e.g., fully differentiated vascular smooth muscle cells in the microvascular wall). Tissue models are typically preferred over cell culture models, because they better reflect the in vivo situation. The experimental model of transfected isolated microvessels may provide a unique framework to translate cell-based knowledge regarding intracellular transport mechanisms into a whole organ system. However, in prior art setups, the use of isolated microvessels requires highly skilled personnel trained in micro-dissection techniques, specialized equipment and substantial time (e.g., for isolation and cannulation processes). The presently disclosed device may facilitate the fundamental experimental procedures and allow for a higher throughput.

Using this device, researchers may more easily and more efficiently use isolated vessels, for example to (i) test new innovations in optical technologies and (ii) identify critical microvascular transport proteins and their regulation patterns in a complex multicellular environment. In combination with access to human tissue, this may allow researchers to be in a position to correlate individual disease patterns (e.g., clinical diagnosis) with alterations in intracellular transport mechanisms in microvessels isolated from patient biopsies.

EXAMPLES

Figure 31:
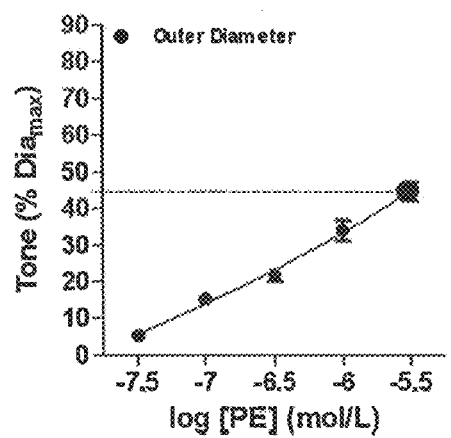
FIG. 31 shows charts illustrating arterial responses to phenylephrine, measured using a device for investigation of a flow conduit.
Figure 31:
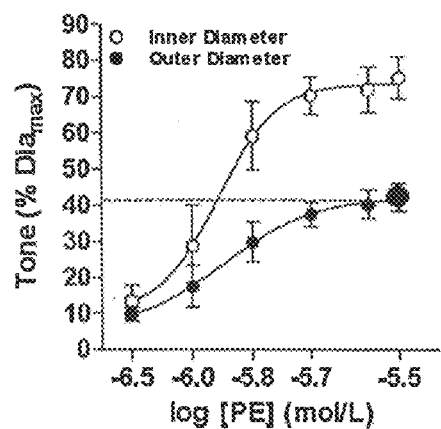

The device may be used to investigate responses of biological flow conduits. It has been found that investigation using the device produces results similar to results produced by other conventional methods. For example, FIG. 31 shows charts illustrating arterial responses to phenylephrine (PE), measured using the device. In this example, PE was applied to the exterior surface of the flow conduit, and the dose of PE was changed in a stepwise fashion. The measured changes in the flow conduit diameter are shown in the charts. a) shows the dose dependent response to PE, measured in mesenteric arteries using a conventional pipette cannulation setup. In this example, the maximal outer diameter constriction was 44.5+/−2.5% at 3.0 µM PE (n=5). b) shows the dose dependent PE response (here, changes in inner and outer diameters of the flow conduit) measured using the device, which are similar to and essentially identical to the results using the conventional cannulation setup, with a maximal outer diameter constriction of 42.2+/−3.8% at 3.0 µM PE (n=5).

Figure 32:
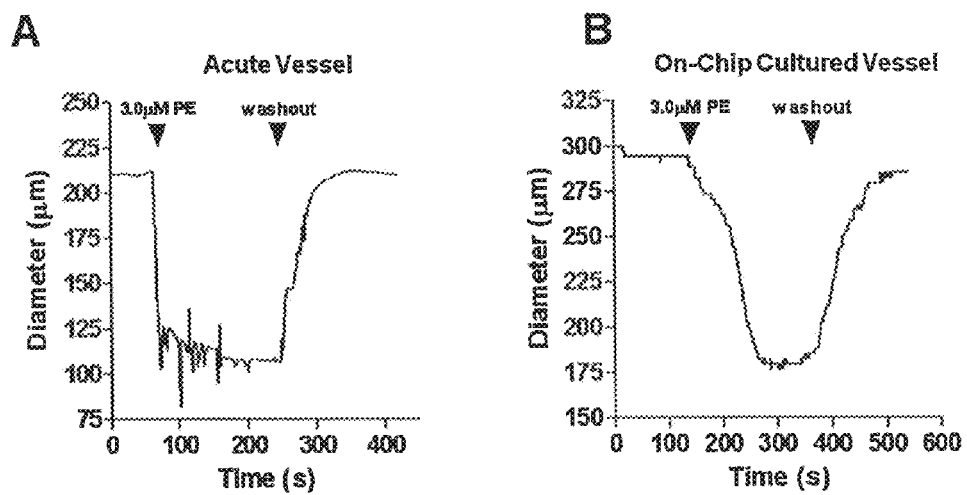
FIG. 32 shows charts illustrating constriction of a mesenteric vessel a device for investigation of a flow conduit.

In another example, the device was used to investigate a mesenteric vessel. FIG. 32 shows charts illustrating constriction of a mesenteric vessel in the device. In this example, a mouse mesenteric vessel was used, and a single does of PE was administered. The PE was applied to the exterior surface of the flow conduit. a) is a representative tracing of a mesenteric vessel's response to 3.0 µM PE, with a sustained constriction of 41.8%, measured in freshly isolated arteries that were immediately subjected to the stimulation with PE. b) is a representative tracing of a single mesenteric vessel kept in culture for 24 hours on the device prior to testing the response to PE, showing a sustained constriction of 41.4% to 3.0 µM PE. The vessel investigated using the device was still viable after 24 hours and did not show a modified response to PE.

Figure 33:
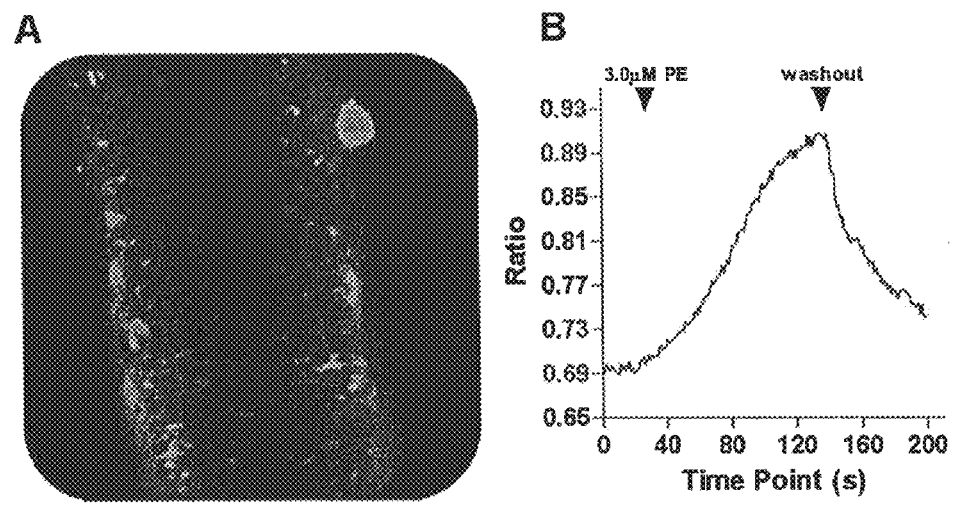
FIG. 33 shows an image and a chart illustrating ratio measurements on an artery in a device for investigation of a flow conduit, It will be noted that throughout the appended drawings, like features are identified by like reference numerals.

FIG. 33 shows a reconstructed fluorescence image and a chart illustrating ratiometric measurements, using a FURA-2 dye, which is a calcium-sensitive dye, on a mesenteric artery in an example embodiment of the device. The smooth muscle cells in the artery are stained. A mouse mesenteric artery was used in this example. a) shows the mesenteric artery fixed on the device, and loaded with FURA-2 $Ca^{2+}$ ratiometric dye, showing smooth muscle cells wrapped around the vessel circumference. b) is a chart showing FURA-2 ratiometric measurements from the fixed vessel, showing an increase in FURA-2 ratio upon stimulation with 3.0 µM PE, and a return to baseline following washout. The chart shows increases in the $F_{340nm}/F_{380nm}$ ratio for FURA-2 in the vessel.

Angiogenesis Assay

The device may also be used to investigate angiogenesis in viable biological flow conduits. For example, the culture chamber may be filled with a biopolymer (e.g., Matrigel™, fibrinogen, etc.), in which a biological conduit, such as a blood vessel, is embedded. The blood vessel may receive culture medium or other compounds by perfusion. Alternatively or in addition, the biopolymer may be superfused by the culture medium or other compounds, and these may then diffuse through the biopolymer to reach the blood vessel. In some cases, a depot of growth factors may be injected at one predefined spot of the biopolymer and allowed to slowly diffuse through the biopolymer. The gradient that is established this way may provide chemotactic guidance to the outgrowing cells of the blood vessel.

As described above, the vessel may be reversibly or irreversibly fixed in the device. Angiogenesis may be induced, for example by subjecting the vessel to angiogenic factors, or by locally injuring the vessel, for example by laser-ablation using a laser-ablation instrument. Healing or angiogenic activity of the vessel may then be observed. Suitable angiogenic factors may include endothelial cell growth factor (ECGF), fibroblast growth factor (FGF), angiogens, low molecular weight endothelial mitogens, endothelial cell chemotactic factors, lipids, vascular endothelial growth factor (VEGF), and platelet-derived growth factor (PDGF).

Other applications may include perfusing the flow conduit with a fluid containing particles or molecules of interest, and assessing transport of the particles or molecules through the wall of the flow conduit and monitoring toxicity.

The device may also be used to investigate the blood-brain barrier. For example, the flow conduit may be a blood vessel from a microvascular network of a brain. Flow conduits that may be investigated include: brain conduits, lung conduits, inner ear conduits, lipid tubules, engineered vessels, hollow fibers, arteries, arterioles, veins, venules, lymphatic vessels, intestines, vas deferens, ovaric tubes, bile duct, bronchial, bronchiole, tracheal conduits, ureter, urethra, pancreatic duct, and kidney tubules, among others. The flow conduit may have a physiological condition to be investigated, for example it may be infarcted, ischemic, inflamed, sclerotic, immune compromised, tumors-bearing, or metastatic. Artificial or engineered flow conduits may also be investigated.

Research and Commercial Applications

Clinical Uses

The translation of knowledge from basic science to clinical application is based on access to human tissues (e.g., analysis of microvessels from biopsies). In order to successfully implement a translational approach, it would be desirable for clinicians to be attracted to the field of microvascular research. Access to human specimens and their respective patient records combined with the disclosed device and state-of-the-art diagnostic technologies may provide opportunities for breakthroughs in understanding and treating microvascular disease. This device may allow standardization of experimental approaches in microvascular research since it may provide: (i) optimized microenvironment for functional vessel analysis and organ culture; (ii) possible automation of the difficult vessel cannulation process; and/or (iii) capability to routinely study very small and fragile arteries. For example, these are useful elements in the construction of a human microcirculatory-based hypertension database, fed by laboratories and hospitals worldwide. The facilitation of the standardized experimental process using this device may attract more clinicians to actively participate.

Treatment Development

This device may provide for high-throughput screening responses at the organ, membrane and vascular conduit levels to treatment of drug products.

Research in blood vessels has the potential to improve quality of life, and increase economic activity. It may help to accelerate the identification of genetic, epigenetic, proteomic, cellular and molecular mechanisms of tone and/or diameter regulation in resistance arteries that predominantly contribute to the regulation of systemic blood pressure. The control of blood pressure is useful to prevent the development of cardiovascular diseases. Understanding its underlying molecular mechanisms may significantly impact the development of new treatment strategies. An improvement of knowledge about hypertension and the related molecular mechanisms may benefit from investigative models that simulate the in vivo situation as accurately as possible. This device may provide such a model. It may help to identify new targets for treatments and may allow for their immediate verification on the same platform. Thus, this device may bring basic science discoveries to their clinical application in less time.

This device may also make fundamental experimental procedures high-throughput ready. Therefore, this device may be an attractive tool for target identification, target validation, drug design and high-throughput screening in the drug development process. This device may be used for investigation of both animal- and human-based specimens. The device may also be used in a diagnostic tool, for example to directly correlate the cardiovascular health status of a given patient to the functional state of his/her microcirculation. This may provide a personalized approach to the diagnosis and specific treatment of microvascular pathologies, thus translating fundamental scientific knowledge into clinical applications. Thus, the device may help to enable personalized medicine.

This device may allow structural and response testing of flow conduits, for example in the identification of treatment products. This device may be used to test flow conduits from animals, humans, plants, and other organisms. The flow conduits may be from any organ, and may also include artificial or engineered conduits. The device may allow for targeted treatment of either an individual or groups of individuals by using their representative conduits in screening for or assessment of certain drugs, diseases, conditions, or treatments.

It is desirable that important life-saving new drug products have quick regulatory approval in order to get to the market. Fast-track clinical trials and registration are critical parts of the process that ensure efficacy and safety. Devices and methodologies to quickly identify target products in screening at a level that is closer representative of in vivo conditions is an area that may facilitate the process. For example, one area in health care that may benefit from a more representative treatment assessment in drug development is in the treatment of hypertension or high blood pressure. This device may provide a platform that satisfies this need.

Similarly, this device may aid in the development of compounds for use in plants and animals, as it provides a platform for testing of experimental or new compounds in various flow conduits.

Training

The disclosed device may allow researchers to target the vascular problems, such as the problem of microvascular dysfunction, its cellular and molecular mechanisms and its inherent risks for the health of the population, as broadly as possible. The involved technology may represent a change of paradigms, and standards in an emerging field of research. It may provide opportunities to recruit and train all levels of research trainees including undergraduate and graduate students in the highly specialized field of microvascular research. The technical and fundamental skills offered by this training are in great demand in universities, life science and medical research institutes, and biotechnical industries.

As described, the device may include variations such as reversible fixation of vessels (e.g., using a suction method) or permanent fixation of vessels (e.g., using a photocurable polymer or tissue glue method). The tubular structures or channels of the device may be lipid tubules, hollow fibers, or other suitable structures. The device may also be designed to be interconnectable in a complex fluid network. The device may be designed with various layouts, with various arrangements of module(s) and channels.

This device may be useful in the pharmaceutical industry for target identification, target validation, molecular drug design and optimization, early stage toxicity test, and/or proof of concept for new drugs. Clinical applications for this device include personalized medicine, isolation of arteries and venules from patient biopsies to determine vasomotor status (e.g., for assessment of structural and functional characteristics of individual vessels including correlation with individual patient history), and pharmacogenetics. The device may also be used to assess the treatment of a targeted individual or group of individuals to a pharmaceutical product or treatment by using the treated flow conduit of the individual or representative group of individuals in the assessment, such as in pharmacogenetics. This device may also be useful in the crop protection industry for high-throughput testing of plants and plant compounds.

The example embodiments of the present disclosure described above are intended to be examples only. Those of skill in the art may effect alterations, modifications and variations to the particular example embodiments without departing from the intended scope of the present disclosure. In particular, selected features from one or more of the above-described example embodiments may be combined to create alternative example embodiments not explicitly described, features suitable for such combinations being readily apparent to persons skilled in the art. The subject matter described herein in the recited claims intends to cover and embrace all suitable changes in technology. All references mentioned are hereby incorporated by reference in their entirety.

What is claimed is:

1. A device for investigation of a substantially tubular biological flow conduit comprising:
    a base having formed: therein
        a loading inlet for loading the flow conduit into the device;
        a main channel for receiving the flow conduit from the loading inlet, the main channel having a flow path along a first directional axis;
        a culture chamber in the main channel
        at least two fixation lines fluidly connected to the main channel for providing fixation of the flow conduit at at least two fixation locations along the length of the flow conduit within the culture chamber so that when fixed the flow conduit is substantially longitudinally aligned with the flow path along the first directional axis;
        the main channel having a perfusion inlet and a perfusion outlet, one of which is located before the at least two fixation lines along the flow path along the first directional axis and the other of which is located after the at least two fixation lines along the flow path along the first directional axis; and
        a superfusion channel fluidly connected to the main channel between the fixation locations, the superfusion channel having a flow path along a second directional axis at the point of connection to the main channel.

2. The device of claim 1, wherein there is a plurality of fixation fluidly connected to the culture chamber.

3. The device of claim 1, wherein a plurality of culture chambers are arranged in series along the first directional axis in the main channel, each culture chamber being fluidly connected to at least two fixation lines.

4. The device of claim 1, wherein a plurality of main channels and culture chambers are arranged in parallel, each culture chamber being fluidly connected to at least two fixation lines, the culture chambers being fluidly connected to a common superfusion channel that intersects each culture chamber at a position between their respective first and second fixation lines.

5. The device of claim 1, further comprising a lysis chamber in the main channel, the lysis chamber being in series with the culture chamber and adapted to receive at least a portion of the flow conduit from the culture chamber.

6. The device of claim 1, wherein the at least two fixation lines allow reversible fixation of the flow conduit.

7. The device of claim 1, wherein the main channel has an outlet for extracting the flow conduit for analysis.

8. The device of claim 1, wherein the device contains active compounds that are released over time, wherein the active compounds are selected from nutrients, dyes, pharmaceutical agents, lysing compounds, enzymes and growth factors.

9. The device of claim 1, further comprising an interface adapted to interface with analytical equipment.

10. The device of claim 1, further comprising at least one of a processor, a memory unit and a temperature control unit.

11. The device of claim 9, wherein the analytical equipment is selected from equipment for performing bright field or fluorescence microscopy techniques, including fluorescence intensity and fluorescence lifetime-based imaging, with optical spectroscopy, on-chip lysis and mass spectrometry.

12. The device of claim 1, wherein the device is a microfluidic device.

13. The device of claim 1, wherein the base is deformable.

14. The device of claim 6, further comprising a vacuum or suction source for applying a vacuum or suction to the fixation lines.

15. The device of claim 1 wherein the superfusion channel comprises a superfusion inlet and a superfusion outlet, both of which are fluidly connected to the main channel between the fixation locations.

16. The device of claim 15, wherein the superfusion inlet and the superfusion outlet are fluidly connected to the main channel on the same side of the first directional axis.

* * * * *